US008119126B2

(12) United States Patent
Kishimoto et al.

(10) Patent No.: US 8,119,126 B2
(45) Date of Patent: Feb. 21, 2012

(54) INHIBITING VASCULARIZATION USING ANTIBODIES TO CXCR4 AND SDF-1

(75) Inventors: Tadamitsu Kishimoto, Tondabayashi (JP); Takashi Nagasawa, Sakai (JP); Kazunobu Tachibana, Sakai (JP)

(73) Assignees: Chugai Seiyaku Kabushiki Kasha, Tokyo (JP); Tadamitsu Kishimoto, Osaka (JP)

( * ) Notice: Subject to any disclaimer, the term of this patent is extended or adjusted under 35 U.S.C. 154(b) by 0 days.

(21) Appl. No.: 10/785,230

(22) Filed: Feb. 25, 2004

(65) Prior Publication Data

US 2004/0209837 A1     Oct. 21, 2004

Related U.S. Application Data

(63) Continuation of application No. 09/646,785, filed as application No. PCT/JP99/01448 on Mar. 23, 1999, now abandoned.

(30) Foreign Application Priority Data

Mar. 24, 1998   (JP) .................................. P10-095448

(51) Int. Cl.
*A61K 39/00*     (2006.01)
*A61K 39/395*    (2006.01)
(52) U.S. Cl. ................... 424/130.1; 424/424; 424/138.1
(58) Field of Classification Search ....... 514/2; 530/350
See application file for complete search history.

(56) References Cited

U.S. PATENT DOCUMENTS

| | | | | |
|---|---|---|---|---|
| 5,378,725 | A |   | 1/1995 | Bonjouklian et al. ........ 514/453 |
| 5,525,625 | A |   | 6/1996 | Bridges et al. ................ 514/456 |
| 5,543,503 | A | * | 8/1996 | Chuntharapai et al. .. 530/388.22 |
| 5,563,048 | A | * | 10/1996 | Honjo et al. ................. 435/69.1 |
| 6,863,887 | B1 | * | 3/2005 | Murphy et al. ............ 424/130.1 |

FOREIGN PATENT DOCUMENTS

| EP | 0666868 B2 | 8/1995 |
|---|---|---|
| EP | 0897980 | 2/1999 |
| JP | 04-224559 | 8/1992 |
| JP | 05-039221 | 2/1993 |
| WO | WO 96/24598 | 8/1996 |

OTHER PUBLICATIONS

Blast data for chemokine receptor CXCR4 (pp. 1-6 from Signaling Gateway).*
Blast data for SDF-1 protein (pp. 1-4 from Signaling Gateway).*
iHOP, Information Hyperlinked over Proteins; p. 1 for CXCR4.*
iHOP, Information Hyperlinked over Proteins; p. 1 for CXCL12.*
Tavor et al, Cancer Research, 2004, 64:2817-2824.*
Bertolini et al (Cancer Research, 2002, 62:3106-3112).*
Butler et al (J of Clinical Investigation, 2005, 115:86-93).*
Sengupta et al (Investigative Ophthalmology & Visual Science, 2005, 46:343-348).*
Walter et al (Circulation Research, 2005, 97:1142-1151).*
Tachibana et al (Nature, 1998, 393:591-594).*
Jiang et al (Gynecologic Oncology, 2006, 103:226-233).*
Marini et al (J of Clinical Oncology, 2007, ASCO Annual Meeting Proceedings Part I, vol. 25, No. 18S, 2007: abstract# 21159).*
White et al. (2001, Ann. Rev. Med., 2001, 52:125-145).*
Arenberg et al (J Clinical Investigation, 1996, 97:2792-2802).*
Strieter et al (J of Leukocyte Biology, 1995, 57: 752-762, IDS).*
Rafii et al (An AACR Special Conference in Cancer Research, Proceedings, Jan. 1998, p. 1-2, IDS).*
Gupta et al (J Biological Chemistry, Feb. 1998, 273: 4282-4287, IDS).*
Volin et al (Biochemical and Biophysical Research Communications, Jan. 1998, 242:46-53, IDS).*
Doranz et al (J Exp Med, Oct. 1997, 186:1395-1400, IDS).*
Doranz et al, J Exp Med, Oct. 1997, 186:1395-1400, IDS).*
In re Alonso, Oct. 2008, US Court of Appeals for the Federal Circuit (p. 1-11 + cover).*
Stancovski et al (PNAS, 1991, 88:8691-8695).*
Volin et al, Biochemical and Biophysical Research Communications, Jan. 1998, 242:46-53, IDS.*
Doranz et al, J Exp Med, Oct. 1997, 186:1395-1400, IDS.*
Arisawa et al., Hepatic Artery Dexamethasone Infusion Inhibits Colorectal Hepatic Metyastases: A Regional Antiangiogenic Therapy, *Ann. Surg. Oncol.* 2:114-120 (Mar. 1995) Raven Press, Ltd., New York, NY, USA.
"Dexamethasone—Indications and Usage" (English translation), p. C-1712, ISBN4-567-01311-5.
Feil et al., Endothelial Cells Differentially Express Functional CXC-Chemokine Receptor-4 (CXCR-4/Fusin) Under the Control of Autocrine Activity and Exogenous Cytokines, *Biochem. Biophy. Res. Commun.* 247:38-45 (Jun. 1998) Academic Press Inc., Orlando, FL, USA. Gupta et al., Selective Functional Expression of CXCR4 (Fusin) in Vascular Endothelial Cells and Transcriptional Regulation by Inflammatory Cytokines, *FASEB J.* 11(9)(suppl.):A1384 (Jul. 1997) Fed. of American Soc. for Experimental Biology, Bethesda, MD, USA.
Gupta et al., Chemokine Receptors in Human Endothelial Cells, *J. Biol. Chem.* 273(7):4282-4287 (Feb. 1998) American Society of Biological Chemists, Baltimore, MD, USA.
Murakami et al., A Small Molecule Inhibitor CXCR4 that Blocks T Cell Line-Tropic HIV-1 Infection, *J. Exp. Med.* 186(8):1389-1393 (Oct. 1997) Rockefeller University Press, New York, NY, USA.
Signoret et al., Phorbol Esters and SDF-1 Induce Rapid Endocytosis and Down Modulation of the Chemokine Receptor CXCR4, *J. Cell Biol.* 193(3):651-664 (Nov. 1997) Rockefeller University Press, New York, NY, USA.
Suzuki et al., Inhibition of Human Immunodeficiency Virus Type-1 Infection by a Recombinant HIV Vector Expressing Antisense-CXCR4, *Blood* 92(10)(suppl. 1):386B, (Nov. 1998) W.B. Saunders, Philadelphia, VA, USA.

(Continued)

*Primary Examiner* — Laura B Goddard
(74) *Attorney, Agent, or Firm* — Morgan, Lewis & Bockius LLP

(57) ABSTRACT

This invention provides a therapeutic agent for inhibiting neovascularization, a therapeutic agent for a solid cancer, a therapeutic agent for a disease pathologically caused by neovascularization, and a therapeutic agent for repairing a tissue comprising as the effective ingredient, a substance that potentiates the action of CXCR4.
Based on the finding that vascularization is suppressed in CXCR4 knockout mice, it becomes possible to prepare a therapeutic agent for suppressing vascularization, a therapeutic agent for a solid cancer, a therapeutic agent for a disease pathologically caused by neovascularization, each of which comprises as the effective ingredient, a substance that inhibits the action of CXCR4, as well as to prepare a therapeutic agent for repairing a tissue comprising as the effective ingredient, a substance that potentiates the action of CXCR4. Methods for treatment are made possible that use these therapeutic agents.

6 Claims, 9 Drawing Sheets

OTHER PUBLICATIONS

Tachibana et al., The Chemokine Receptor CXCR4 is Essential for Vascularization of the Gastrointestinal Tract, *Nature* 393:591-594 (Jun. 1998) MacMillan Journals Ltd., London, GB.

Volin et al., Chemokine Receptor CXCR4 Expression in Endothelium, *Biochem. Biophys. Res. Commun.* 242:46-53 (Jan. 1998) Academic Press Inc., Orlando, FL, USA.

Communication of Notice of Opposition for EP 99909307.3 filed by Eli Lily and Company dated May 2, 2007.

Communication of Notice of Opposition for EP 99909307.3 filed by Strawman Limited dated May 2, 2007.

Bleul et al. (1997), The HIV corecptors CXCR4 and CCRG are differentially expressed and regulated on human T lymphocytes, Proc. Natl. Acad. Sic. USA 94: 1925-1930.

Donzella et al. (1998), AMD3100, a small molecule inhibitor of HIV-1 entry via the CXCR4 co-receptor, Nature Medicine 4: 72-77.

Doranz et al. (1997), A Small-molecule Inhibitor Directed against a Chemokine Receptor CXCR4 Prevents its Use as an HIV-1 Coreceptor, J. Exp. Med. 8: 1395-1400.

Eliceiri et al. (1998) Integrin αvβ3 Requirement for Sustained Mitogen-activated Protein Kinase Activity during Angiogenesis, J. Cell. Biol. 140: 1255-1263.

Felszeghy et al. (2004) Dexamethasone Downregulates Chemokine Receptor CXCR4 and Exerts Neuroprotection against Hypoxia/Ischemia-Induced Brain Injury in Neonatal Rats, Neuroimmunomodulation 11: 404-413.

Gupta et al. (1998), Chemokine Receptors in Human Endothelial Cells, J. Biol Chem. 273: 4282-4287.

Hanahan et al. (1998), Patterns and Emerging Mechanisms of the Angiogenic Switch during Tumorgenesis, Cell 86: 352-364.

Jackson et al. (1998) Pharmacological Effects of SB 220025, a Selective Inhibitor of P38 Mitogen-Activated Protein Kinase, in Angiogenesis and Chronic Inflammatory Disease Models, J. Pharmacol. Exp. Therapeut. 284: 687-692.

Murakami et al. (1997) A Small Molecule CXCRA Inhibitor that Blocks T Cell Line-tropic HIV-1 Infection, J. Exp. Med. 186: 1389-1393.

Oikawa et al. (1996) Potent inhibition of angiogenesis by wortmannin, a fungal metabolite, European Journal of Pharmacology 318: 93-96.

Rafii et al. (1998) Regulation of Trafficking of Bone-Marrow Derived CD34+KDR+ Endothelial Progenitor Cells, Angiogenesis and Cancer, Proceedings AACR Special Conference in Cancer Research.

Schols et al. (1997), Inhibition of T-tropic HIV Strains by Selective Antagonization of the Chemokine Receptor CXCR4, J. Exp. Med. 186: 1383-1388.

Stedmans Medical Dictionary, 26th Ed. (1995), 85, 1182, 1909.

Strieter et al. (1995) Role of C-X-C chemokines as regulators of angiogenesis in lung cancer, J. Leukocyte Biol. 57: 752-761.

Whalen (1990), Solid tumours and wounds: transformed cells misunderstood as injured tissue?, The Lancet 336: 1489-1492.

Moore et al. (1998), The Role of CXC Chemokines in the Regulation of Angiogenesis in Association with Lung Cancer, TCMS 8: 51-58.

Strieter et al. (1995), The Functional Role of the ELR Motif in CXC Chemokine-mediated Angiogenesis, J. Biol. Chem. 270: 27348-357.

Aluti et al. (1997), The chemokine SDF-1 is a chemoattractant for human CD34+ hematopoietic progenitor cells and provides a new mechanism to explain the mobilization of CD34+ progenitors to peripheral blood, J. Exp Med. 185:111-20.

Amara et al. (1997), HIV coreceptor downregulation as antiviral principle: SDF-1 alpha-dependent internalization of the chemokine receptor CXCR4 contributes to inhibition of HIV replication, J. Exp Med. 186:139-46.

Asahara et al. (1997), Isolation of putative progenitor endothelial cells for angiogenesis, Science 275:964-7.

Bouck et al. (1996), How tumors become angiogenic, Adv Cancer Res. 69:135-74.

Carmeliet (1996), Abnormal blood vessel development and lethality in embryos lacking a single VEGF allele, Nature 380:435-9.

Carmeliet P, Jain RK. (2000), Angiogenesis in cancer and other diseases, Nature 407:249-57.

Chen et al. (2003), Down-regulation of CXCR4 by inducible small interfering RNA inhibits breast cancer cell invasion in Vitro, Cancer Res. 63:4801-4.

Ferrara et al. (1996), Heterozygous embryonic lethality induced by targeted inactivation of the VEGF gene, Nature 380:439-42.

Folkman, J. (1971), Tumor angiogenesis: Therapeutic Implications. New Engl. J. Med. 285:1182-6.

Folkman, J. (1990), What is the evidence that tumors are angiogenesis dependent? J. Natl Cancer Inst. 82:4-6.

Haeberlin et al. (1993), In vitro evaluation of dexamethasone-beta-D-glucuronide for colon-specific drug delivery, Pharm Res. 10:1553-62.

Leon, L. (2005), Invited review: The use of gene knockout mice in thermoregulation studies, J. Thermal Biol. 30:273-88.

Ma et al. (1998), Impaired B-lymphopoiesis, myelopoiesis, and derailed cerebellar neuron migration in CXCR4- and SDF-1-deficient mice, Proc Natl Acad Sci USA 95:9448-53.

Müller, U. (1999), Ten years of gene targeting: targeted mouse mutants, from vector design to phenotype analysis. Mechanism of Development 82:3-21.

Shalaby et al. (1995), Failure of blood-island formation and vasculogenesis in Flk-1-deficient mice, Nature 376: 62-6.

Smith et al. (2004), CXCR4 regulates growth of both primary and metastatic breast cancer, Cancer Res. 64: 8604-12.

Spano et al. (2004), Chemokine receptor CXCR4 and early-stage non-small cell lung cancer: pattern of expression and correlation with outcome, Ann Oncol. 15:613-7.

Weis et al. (2008), Compensatory role for Pyk2 during angiogenesis in adult mice lacking endothelial cell FAK, J. Cell Biol. 181:43-50.

Zou et al. (1998), Function of the chemokine receptor CXCR4 in haematopoiesis and in cerebellar development, Nature 393:524-5.

* cited by examiner

Figure 13A  Figure 13B  Figure 13C
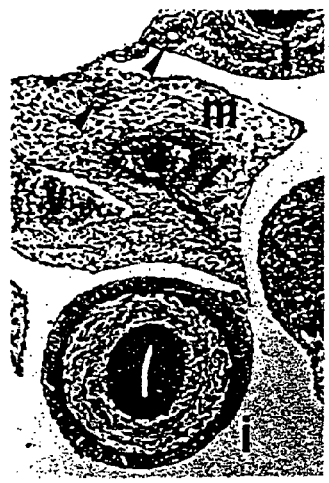  
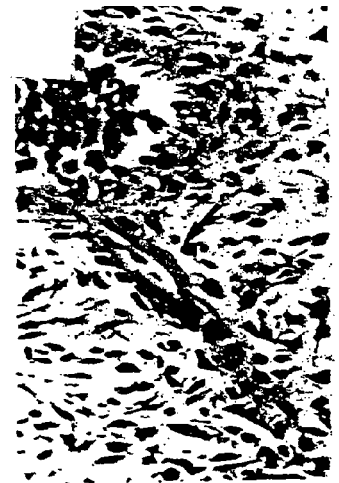  
Figure 13D  Figure 13E  Figure 13F

SEQUENCE LISTING

<160> NUMBER OF SEQ ID NOS: 12

<210> SEQ ID NO 1
<211> LENGTH: 352
<212> TYPE: PRT
<213> ORGANISM: Homo sapiens

<400> SEQUENCE: 1

```
Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
```

|     |     |     |     |     |     |     |     |     |     |     |     |     |
| --- | --- | --- | --- | --- | --- | --- | --- | --- | --- | --- | --- | --- |
|     |     | 325 |     |     |     | 330 |     |     |     | 335 |     |     |
| His | Ser | Ser | Val | Ser | Thr | Glu | Ser | Glu | Ser | Ser | Ser | Phe | His | Ser | Ser |
|     |     |     | 340 |     |     |     | 345 |     |     |     | 350 |     |

<210> SEQ ID NO 2
<211> LENGTH: 1588
<212> TYPE: DNA
<213> ORGANISM: Homo sapiens
<220> FEATURE:
<221> NAME/KEY: CDS
<222> LOCATION: (1)..(1059)

<400> SEQUENCE: 2

```
atg gag ggg atc agt ata tac act tca gat aac tac acc gag gaa atg        48
Met Glu Gly Ile Ser Ile Tyr Thr Ser Asp Asn Tyr Thr Glu Glu Met
1               5                   10                  15 ggc tca ggg gac tat gac tcc atg aag gaa ccc tgt ttc cgt gaa gaa        96
Gly Ser Gly Asp Tyr Asp Ser Met Lys Glu Pro Cys Phe Arg Glu Glu
                20                  25                  30 aat gct aat ttc aat aaa atc ttc ctg ccc acc atc tac tcc atc atc       144
Asn Ala Asn Phe Asn Lys Ile Phe Leu Pro Thr Ile Tyr Ser Ile Ile
            35                  40                  45 ttc tta act ggc att gtg ggc aat gga ttg gtc atc ctg gtc atg ggt       192
Phe Leu Thr Gly Ile Val Gly Asn Gly Leu Val Ile Leu Val Met Gly
        50                  55                  60 tac cag aag aaa ctg aga agc atg acg gac aag tac agg ctg cac ctg       240
Tyr Gln Lys Lys Leu Arg Ser Met Thr Asp Lys Tyr Arg Leu His Leu
65                  70                  75                  80 tca gtg gcc gac ctc ctc ttt gtc atc acg ctt ccc ttc tgg gca gtt       288
Ser Val Ala Asp Leu Leu Phe Val Ile Thr Leu Pro Phe Trp Ala Val
                85                  90                  95 gat gcc gtg gca aac tgg tac ttt ggg aac ttc cta tgc aag gca gtc       336
Asp Ala Val Ala Asn Trp Tyr Phe Gly Asn Phe Leu Cys Lys Ala Val
                100                 105                 110 cat gtc atc tac aca gtc aac ctc tac agc agt gtc ctc atc ctg gcc       384
His Val Ile Tyr Thr Val Asn Leu Tyr Ser Ser Val Leu Ile Leu Ala
            115                 120                 125 ttc atc agt ctg gac cgc tac ctg gcc atc gtc cac gcc acc aac agt       432
Phe Ile Ser Leu Asp Arg Tyr Leu Ala Ile Val His Ala Thr Asn Ser
        130                 135                 140 cag agg cca agg aag ctg ttg gct gaa aag gtg gtc tat gtt ggc gtc       480
Gln Arg Pro Arg Lys Leu Leu Ala Glu Lys Val Val Tyr Val Gly Val
145                 150                 155                 160 tgg atc cct gcc ctc ctg ctg act att ccc gac ttc atc ttt gcc aac       528
Trp Ile Pro Ala Leu Leu Leu Thr Ile Pro Asp Phe Ile Phe Ala Asn
                165                 170                 175 gtc agt gag gca gat gac aga tat atc tgt gac cgc ttc tac ccc aat       576
Val Ser Glu Ala Asp Asp Arg Tyr Ile Cys Asp Arg Phe Tyr Pro Asn
                180                 185                 190 gac ttg tgg gtg gtt gtg ttc cag ttt cag cac atc atg gtt ggc ctt       624
Asp Leu Trp Val Val Val Phe Gln Phe Gln His Ile Met Val Gly Leu
            195                 200                 205 atc ctg cct ggt att gtc atc ctg tcc tgc tat tgc att atc tcc           672
Ile Leu Pro Gly Ile Val Ile Leu Ser Cys Tyr Cys Ile Ile Ser
        210                 215                 220 aag ctg tca cac tcc aag ggc cac cag aag cgc aag gcc ctc aag acc       720
Lys Leu Ser His Ser Lys Gly His Gln Lys Arg Lys Ala Leu Lys Thr
225                 230                 235                 240 aca gtc atc ctc atc ctg gct ttc ttc gcc tgt tgg ctg cct tac tac       768
Thr Val Ile Leu Ile Leu Ala Phe Phe Ala Cys Trp Leu Pro Tyr Tyr
                245                 250                 255
```

```
att ggg atc agc atc gac tcc ttc atc ctc ctg gaa atc atc aag caa      816
Ile Gly Ile Ser Ile Asp Ser Phe Ile Leu Leu Glu Ile Ile Lys Gln
        260                 265                 270 ggg tgt gag ttt gag aac act gtg cac aag tgg att tcc atc acc gag      864
Gly Cys Glu Phe Glu Asn Thr Val His Lys Trp Ile Ser Ile Thr Glu
    275                 280                 285 gcc cta gct ttc ttc cac tgt tgt ctg aac ccc atc ctc tat gct ttc      912
Ala Leu Ala Phe Phe His Cys Cys Leu Asn Pro Ile Leu Tyr Ala Phe
        290                 295                 300 ctt gga gcc aaa ttt aaa acc tct gcc cag cac gca ctc acc tct gtg      960
Leu Gly Ala Lys Phe Lys Thr Ser Ala Gln His Ala Leu Thr Ser Val
305                 310                 315                 320 agc aga ggg tcc agc ctc aag atc ctc tcc aaa gga aag cga ggt gga     1008
Ser Arg Gly Ser Ser Leu Lys Ile Leu Ser Lys Gly Lys Arg Gly Gly
                325                 330                 335 cat tca tct gtt tcc act gag tct gag tct tca agt ttt cac tcc agc     1056
His Ser Ser Val Ser Thr Glu Ser Glu Ser Ser Ser Phe His Ser Ser
                340                 345                 350 taa cacagatgta aaagactttt ttttatacga taaataactt ttttttaagt          1109
tacacatttt tcagatataa aagactgacc aatattgtac agttttatt gcttgttgga    1169 tttttgtctt gtgtttcttt agttttgtg aagtttaatt gacttattta tataaattttt   1229 ttttgtttca tattgatgtg tgtctaggca ggacctgtgg ccaagttctt agttgctgta   1289
tgtctcgtgg taggactgta gaaaagggaa ctgaacattc cagagcgtgt agttaatcac   1349
gtaaagctag aaatgatccc cagctgttta tgcatagata atctctccat tcccgtggaa   1409 cgttttcct gttcttaaga cgtgattttg ctgtagaaga tggcacttat aaccaaagcc    1469
caaagtggta tagaaatgct ggttttcag ttttcaggag tgggttgatt tcagcaccta    1529
cagtgtacag tcttgtatta agttgttaat aaaagtacat gttaaactta aaaaaaaaa    1588
```

<210> SEQ ID NO 3
<211> LENGTH: 359
<212> TYPE: PRT
<213> ORGANISM: Mus musculus

<400> SEQUENCE: 3

```
Met Glu Pro Ile Ser Val Ser Ile Tyr Thr Ser Asp Asn Tyr Ser Glu
1               5                   10                  15

Glu Val Gly Ser Gly Asp Tyr Asp Ser Asn Lys Glu Pro Cys Phe Arg
            20                  25                  30

Asp Glu Asn Val His Phe Asn Arg Ile Phe Leu Pro Thr Ile Tyr Phe
        35                  40                  45

Ile Ile Phe Leu Thr Gly Ile Val Gly Asn Gly Leu Val Ile Leu Val
    50                  55                  60

Met Gly Tyr Gln Lys Lys Leu Arg Ser Met Thr Asp Lys Tyr Arg Leu
65                  70                  75                  80

His Leu Ser Val Ala Asp Leu Leu Phe Val Ile Thr Leu Pro Phe Trp
                85                  90                  95

Ala Val Asp Ala Met Ala Asp Trp Tyr Phe Gly Lys Phe Leu Cys Lys
            100                 105                 110

Ala Val His Ile Ile Tyr Thr Val Asn Leu Tyr Ser Ser Val Leu Ile
        115                 120                 125

Leu Ala Phe Ile Ser Leu Asp Arg Tyr Leu Ala Ile Val His Ala Thr
    130                 135                 140

Asn Ser Gln Arg Pro Arg Lys Leu Leu Ala Glu Lys Ala Val Tyr Val
145                 150                 155                 160
```

```
Gly Val Trp Ile Pro Ala Leu Leu Leu Thr Ile Pro Asp Phe Ile Phe
                165                 170                 175

Ala Asp Val Ser Gln Gly Asp Ile Ser Gln Gly Asp Arg Tyr Ile
        180                 185                 190

Cys Asp Arg Leu Tyr Pro Asp Ser Leu Trp Met Val Phe Gln Phe
        195                 200                 205

Gln His Ile Met Val Gly Leu Ile Leu Pro Gly Ile Val Ile Leu Ser
        210                 215                 220

Cys Tyr Cys Ile Ile Ile Ser Lys Leu Ser His Ser Lys Gly His Gln
225                 230                 235                 240

Lys Arg Lys Ala Leu Lys Thr Thr Val Ile Leu Ile Leu Ala Phe Phe
                245                 250                 255

Ala Cys Trp Leu Pro Tyr Tyr Val Gly Ile Ser Ile Asp Ser Phe Ile
                260                 265                 270

Leu Leu Gly Val Ile Lys Gln Gly Cys Asp Phe Glu Ser Ile Val His
            275                 280                 285

Lys Trp Ile Ser Ile Thr Glu Ala Leu Ala Phe Phe His Cys Cys Leu
        290                 295                 300

Asn Pro Ile Leu Tyr Ala Phe Leu Gly Ala Lys Phe Lys Ser Ser Ala
305                 310                 315                 320

Gln His Ala Leu Asn Ser Met Ser Arg Gly Ser Ser Leu Lys Ile Leu
                325                 330                 335

Ser Lys Gly Lys Arg Gly Gly His Ser Ser Val Ser Thr Glu Ser Glu
                340                 345                 350

Ser Ser Ser Phe His Ser Ser
            355

<210> SEQ ID NO 4
<211> LENGTH: 1758
<212> TYPE: DNA
<213> ORGANISM: Mus musculus
<220> FEATURE:
<221> NAME/KEY: CDS
<222> LOCATION: (1)..(1080)

<400> SEQUENCE: 4 atg gaa ccg atc agt gtg agt ata tac act tct gat aac tac tct gaa     48
Met Glu Pro Ile Ser Val Ser Ile Tyr Thr Ser Asp Asn Tyr Ser Glu
1               5                   10                  15 gaa gtg ggg tct gga gac tat gac tcc aac aag gaa ccc tgc ttc cgg     96
Glu Val Gly Ser Gly Asp Tyr Asp Ser Asn Lys Glu Pro Cys Phe Arg
            20                  25                  30 gat gaa aac gtc cat ttc aat agg atc ttc ctg ccc acc atc tac ttc    144
Asp Glu Asn Val His Phe Asn Arg Ile Phe Leu Pro Thr Ile Tyr Phe
        35                  40                  45 atc atc ttc ttg act ggc ata gtc ggc aat gga ttg gtg atc ctg gtc    192
Ile Ile Phe Leu Thr Gly Ile Val Gly Asn Gly Leu Val Ile Leu Val
    50                  55                  60 atg ggt tac cag aag aag cta agg agc atg acg gac aag tac cgg ctg    240
Met Gly Tyr Gln Lys Lys Leu Arg Ser Met Thr Asp Lys Tyr Arg Leu
65                  70                  75                  80 cac ctg tca gtg gct gac ctc ctc ttt gtc atc aca ctc ccc ttc tgg    288
His Leu Ser Val Ala Asp Leu Leu Phe Val Ile Thr Leu Pro Phe Trp
                85                  90                  95 gca gtt gat gcc atg gct gac tgg tac ttt ggg aaa ttt ttg tgt aag    336
Ala Val Asp Ala Met Ala Asp Trp Tyr Phe Gly Lys Phe Leu Cys Lys
            100                 105                 110 gct gtc cat atc atc tac act gtc aac ctc tac agc agc gtt ctc atc    384
Ala Val His Ile Ile Tyr Thr Val Asn Leu Tyr Ser Ser Val Leu Ile
        115                 120                 125
```

```
                115                     120                     125
ctg gcc ttc atc agc ctg gac cgg tac ctc gcc att gtc cac gcc acc    432
Leu Ala Phe Ile Ser Leu Asp Arg Tyr Leu Ala Ile Val His Ala Thr
    130                     135                     140 aac agt caa agg cca agg aaa ctg ctg gct gaa aag gca gtc tat gtg    480
Asn Ser Gln Arg Pro Arg Lys Leu Leu Ala Glu Lys Ala Val Tyr Val
145                     150                     155                 160 ggc gtc tgg atc cca gcc ctc ctg act ata cct gac ttc atc ttt        528
Gly Val Trp Ile Pro Ala Leu Leu Leu Thr Ile Pro Asp Phe Ile Phe
                165                     170                     175 gcc gac gtc agc cag ggg gac atc agt cag ggg gat gac agg tac atc    576
Ala Asp Val Ser Gln Gly Asp Ile Ser Gln Gly Asp Asp Arg Tyr Ile
            180                     185                     190 tgt gac cgc ctt tac ccc gat agc ctg tgg atg gtg gtg ttt caa ttc    624
Cys Asp Arg Leu Tyr Pro Asp Ser Leu Trp Met Val Val Phe Gln Phe
        195                     200                     205 cag cat ata atg gtg ggt ctc atc ctg ccc ggc atc gtc atc ctc tcc    672
Gln His Ile Met Val Gly Leu Ile Leu Pro Gly Ile Val Ile Leu Ser
    210                     215                     220 tgt tac tgc atc atc atc tct aag ctg tca cac tcc aag ggc cac cag    720
Cys Tyr Cys Ile Ile Ile Ser Lys Leu Ser His Ser Lys Gly His Gln
225                     230                     235                 240 aag cgc aag gcc ctc aag acg aca gtc atc ctc atc cta gct ttc ttt    768
Lys Arg Lys Ala Leu Lys Thr Thr Val Ile Leu Ile Leu Ala Phe Phe
                245                     250                     255 gcc tgc tgg ctg cca tat tat gtg ggg atc agc atc gac tcc ttc atc    816
Ala Cys Trp Leu Pro Tyr Tyr Val Gly Ile Ser Ile Asp Ser Phe Ile
            260                     265                     270 ctt ttg gga gtc atc aag caa gga tgt gac ttc gag agc att gtg cac    864
Leu Leu Gly Val Ile Lys Gln Gly Cys Asp Phe Glu Ser Ile Val His
        275                     280                     285 aag tgg atc tcc atc aca gag gcc ctc gcc ttc ttc cac tgt gcc ctg    912
Lys Trp Ile Ser Ile Thr Glu Ala Leu Ala Phe Phe His Cys Cys Leu
    290                     295                     300 aac ccc atc ctc tat gcc ttc ctc ggg gcc aag ttc aaa agc tct gcc    960
Asn Pro Ile Leu Tyr Ala Phe Leu Gly Ala Lys Phe Lys Ser Ser Ala
305                     310                     315                 320 cag cat gca ctc aac tcc atg agc aga ggc tcc agc ctc aag atc ctt   1008
Gln His Ala Leu Asn Ser Met Ser Arg Gly Ser Ser Leu Lys Ile Leu
                325                     330                     335 tcc aaa gga aag cgg ggt gga cac tct tcc gtc tcc acg gag tca gaa   1056
Ser Lys Gly Lys Arg Gly Gly His Ser Ser Val Ser Thr Glu Ser Glu
            340                     345                     350 tcc tcc agt ttt cac tcc agc taa cccttatgca aagacttata taatatat    1110
Ser Ser Ser Phe His Ser Ser
        355 atatatatga taaagaactt ttttatgtta cacattttcc agatataaga gactgaccag   1170 tcttgtacag ttttttttt tttttaattg actgttggga gttatgttc ctctagtttt    1230 tgtgaggttt gacttaattt atataaatat tgttttttgt ttgtttcatg tgaatgagcg   1290 tctaggcagg acctgtggcc aagttcttag tagctgttta tctgtgtgta ggactgtaga   1350 actgtagagg aagaaactga acattccaga atgtgtggta aattgaataa agctagccgt   1410 gatcctcagc tgttgctgca taatctcttc attccgagga gcaccccacc cccaccccca   1470 cccccacccc attcttaaat tgtttggtta tgctgtgtga tggtttgttt ggttttttt    1530 tgttgttgtt gttgtttttt ttttctgtaa aagatggcac ttaaaaccaa agcctgaaat   1590 ggtggtagaa atgctggggt tttttttgtt tgtttgtttt ttcagttttc aagagtagat   1650
```

-continued

```
tgacttcagt ccctacaaat gtacagtctt gtattacatt gttaataaaa gtcaatgata    1710
aacttaaaaa aaaaaaaaaa aaaaaaaaaa aaaaaaaaaa aaaaaaaa                 1758
```

<210> SEQ ID NO 5
<211> LENGTH: 89
<212> TYPE: PRT
<213> ORGANISM: Artificial Sequence
<220> FEATURE:
<223> OTHER INFORMATION: Ligand peptide - Human SDF-1-alpha

<400> SEQUENCE: 5

```
Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85
```

<210> SEQ ID NO 6
<211> LENGTH: 2244
<212> TYPE: DNA
<213> ORGANISM: Homo sapiens
<220> FEATURE:
<221> NAME/KEY: CDS
<222> LOCATION: (471)..(743)

<400> SEQUENCE: 6

```
gcacgggaca ggcccgggcca cacccaccgg ggcgagctcg gagggcggcg ctctgggcgg    60
agggcccggc ggctcggccc agggcgcgtt acctcgtcgc cggggccgga gagggcgggc   120
ggaggcacgg ggcctggagg cgccaggcgg aggatgcggg cgacacggtg gcggcggcga   180
ccgcgcgacc gggcgggcgg gcgggcaggg gcgagcggag ggagggagcg gactgcggca   240
ggatctgtcg aggaaaaatc ttgcggccgg cgattccccg cctttttaagc gcagcctgca   300 ctccccccac cccacgcagg ggcgggcctt ccccaacgcg ggcgcccact ggccgccgcg   360
cgccgctccc ctccagctcg cctgcgcctc tcactctccg tcagccgcat tgcccgctcg   420
gcgtccggcc cccgacccgc gctcgtccgc ccgcccgccc gccgcccgc gcc atg        476
                                                            Ala Met
                                                                1
```

```
aac gcc aag gtc gtg gtc gtg ctg gtc ctc gtg ctg acc gcg ctc tgc    524
Asn Ala Lys Val Val Val Val Leu Val Leu Val Leu Thr Ala Leu Cys
        5                   10                  15 ctc agc gac ggg aag ccc gtc agc ctg agc tac aga tgc cca tgc cga    572
Leu Ser Asp Gly Lys Pro Val Ser Leu Ser Tyr Arg Cys Pro Cys Arg
    20                  25                  30 ttc ttc gaa agc cat gtt gcc aga gcc aac gtc aag cat ctc aaa att    620
Phe Phe Glu Ser His Val Ala Arg Ala Asn Val Lys His Leu Lys Ile
35                  40                  45                  50 ctc aac act cca aac tgt gcc ctt cag att gta gcc cgg ctg aag aac    668
Leu Asn Thr Pro Asn Cys Ala Leu Gln Ile Val Ala Arg Leu Lys Asn
                55                  60                  65 aac aac aga caa gtg tgc att gac ccg aag cta aag tgg att cag gag    716
Asn Asn Arg Gln Val Cys Ile Asp Pro Lys Leu Lys Trp Ile Gln Glu
            70                  75                  80
```

-continued

```
tac ctg gag aaa gct tta aac aag taa gcacaacagc caaaaggac         763
Tyr Leu Glu Lys Ala Leu Asn Lys
         85                  90 tttccgctag acccactcga ggaaaactaa aaccttgtga gagatgaaag ggcaaagacg  823
tgggggaggg ggccttaacc atgaggacca ggtgtgtgtg tggggtgggc acattgatct  883
gggatcgggc ctgaggtttg ccagcattta gaccctgcat ttatagcata cggtatgata  943
ttgcagctta tattcatcca tgccctgtac ctgtgcacgt tggaattttt attactgggg 1003
tttttctaag aaagaaattg tattatcaac agcattttca agcagttagt tccttcatga 1063
tcatcacaat catcatcatt ctcattctca tttttaaat caacgagtac ttcaagatct  1123
gaatttggct tgtttggagc atctcctctg ctcccctggg gagtctgggc acagtcaggt 1183
ggtggcttaa cagggagctg gaaaaagtgt cctttcttca gacactgagg ctcccgcagc 1243
agcgcccctc ccaagaggaa ggcctctgtg gcactcagat accgactggg gctgggcgcc 1303
gccactgcct tcacctcctc tttcaacctc agtgattggc tctgtgggct ccatgtagaa 1363
gccactatta ctgggactgt gctcagagac ccctctccca gctattccta ctctctcccc 1423
gactccgaga gcatgcatta atcttgcttc tgcttctcat ttctgtagcc tgatcagcgc 1483
cgcaccagcc gggaagaggg tgattgctgg ggctcgtgcc ctgcatccct ctcctcccag 1543
ggcctgcccc acagctcggg ccctctgtga gatccgtctt tggcctcctc cagaatggag 1603
ctggccctct cctggggatg tgtaatggtc cccctgctta cccgcaaaag acaagtcttt 1663
acagaatcaa atgcaatttt aaatctgaga gctcgctttg agtgactggg ttttgtgatt 1723
gcctctgaag cctatgtatg ccatggaggc actaacaaac tctgaggttt ccgaaatcag 1783
aagcgaaaaa atcagtgaat aaaccatcat cttgccacta cccccctcctg aagccacagc 1843
agggtttcag gttccaatca gaactgttgg caaggtgaca tttccatgca taaatgcgat 1903
ccacagaagg tcctggtggt atttgtaact ttttgcaagg cattttttta tatatatttt 1963
tgtgcacatt ttttttacg tttctttaga aaacaaatgt atttcaaaat atatttatag 2023
tcgaacaatt catatatttg aagtggagcc atatgaatgt cagtagttta tacttctcta 2083
ttatctcaaa ctactggcaa tttgtaaaga aatatatatg atatataaat gtgattgcag 2143
cttttcaatg ttagccacag tgtattttt cacttgtact aaaattgtat caaatgtgac 2203
attatatgca ctagcaataa aatgctaatt gtttcatggt a                    2244
```

<210> SEQ ID NO 7
<211> LENGTH: 89
<212> TYPE: PRT
<213> ORGANISM: Artificial Sequence
<220> FEATURE:
<223> OTHER INFORMATION: Ligand peptide - Murine SDF-1-alpha

<400> SEQUENCE: 7

```
Met Asp Ala Lys Val Val Ala Val Leu Ala Leu Val Leu Ala Ala Leu
1               5                   10                  15

Cys Ile Ser Asp Gly Lys Pro Val Ser Leu Ser Tyr Arg Cys Pro Cys
            20                  25                  30

Arg Phe Phe Glu Ser His Ile Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80
```

Glu Tyr Leu Glu Lys Ala Leu Asn Lys
                85

<210> SEQ ID NO 8
<211> LENGTH: 1781
<212> TYPE: DNA
<213> ORGANISM: Mus musculus
<220> FEATURE:
<221> NAME/KEY: CDS
<222> LOCATION: (82)..(351)

<400> SEQUENCE: 8

```
gaccactttc cctctcggtc cacctcggtg tcctcttgct gtccagctct gcagcctccg      60
gcgcgccctc ccgcccacgc c atg gac gcc aag gtc gtc gcc gtg ctg gcc       111
                         Met Asp Ala Lys Val Val Ala Val Leu Ala
                           1               5                  10 ctg gtg ctg gcc gcg ctc tgc atc agt gac ggt aaa cca gtc agc ctg       159
Leu Val Leu Ala Ala Leu Cys Ile Ser Asp Gly Lys Pro Val Ser Leu
             15                  20                  25 agc tac cga tgc ccc tgc cgg ttc ttc gag agc cac atc gcc aga gcc       207
Ser Tyr Arg Cys Pro Cys Arg Phe Phe Glu Ser His Ile Ala Arg Ala
         30                  35                  40 aac gtc aag cat ctg aaa atc ctc aac act cca aac tgt gcc ctt cag       255
Asn Val Lys His Leu Lys Ile Leu Asn Thr Pro Asn Cys Ala Leu Gln
     45                  50                  55 att gtt gca cgg ctg aag aac aac aac aga caa gtg tgc att gac ccg       303
Ile Val Ala Arg Leu Lys Asn Asn Asn Arg Gln Val Cys Ile Asp Pro
 60                  65                  70 aaa tta aag tgg atc caa gag tac ctg gag aaa gct tta aac aag taa       351
Lys Leu Lys Trp Ile Gln Glu Tyr Leu Glu Lys Ala Leu Asn Lys
 75                  80                  85 gcacaacagc ccaaaggact tccagtaga ccccgagga aggctgacat ccgtgggaga       411
tgcaagggca gtggtgggga ggagggcctg aaccctggcc aggatggccg gcggacagc      471
actgactggg gtcatgctaa ggtttgccag cataaagaca ctccgccata gcatatggta     531
cgatattgca gcttatattc atccctgccc tcgcccgtgc acaatggagc ttttataact     591
ggggttttc taaggaattg tattacccta accagttagc ttcatcccca ttctcctcat      651
cctcatcttc attttaaaaa gcagtgatta cttcaagggc tgtattcagt ttgctttgga    711
gcttctcttt gccctggggc ctctgggcac agttatagac ggtggctttg cagggagccc    771
tagagagaaa ccttccacca gagcagagtc cgaggaacgc tgcagggctt gtcctgcagg    831
gggcgctcct cgacagatgc cttgtcctga gtcaacacaa gatccggcag agggaggctc    891
ctttatccag ttcagtgcca gggtcgggaa gcttccttta gaagtgatcc ctgaagctgt    951
gctcagagac cctttcctag ccgttcctgc tctctgcttg cctccaaacg catgcttcat   1011
ctgacttccg cttctcacct ctgtagcctg acggaccaat gctgcaatgg aagggaggag   1071
agtgatgtgg ggtgccccct ccctctcttc cctttgcttt cctctcactt gggcccttg    1131
tgagattttt ctttggcctc ctgtagaatg gagccagacc atcctggata atgtgagaac   1191
atgcctagat ttaccacaa acacaagtc tgagaattaa tcataaacgg aagtttaaat     1251
gaggatttgg accttggtaa ttgtccctga gtcctatata tttcaacagt ggctctatgg   1311
gctctgatcg aatatcagtg atgaaaataa taataataat aataataacg aataagccag   1371
aatcttgcca tgaagccaca gtggggattc tgggttccaa tcagaaatgg agacaagata   1431
aaacttgcat acattcttat gatcacagac ggccctggtg gttttggta actatttaca    1491
aggcattttt ttacatatat ttttgtgcac tttttatgtt tctttggaag acaaatgtat   1551
```

-continued

```
ttcagaatat atttgtagtc aattcatata tttgaagtgg agccatagta atgccagtag      1611
atatctctat gatcttgagc tactggcaac ttgtaaagaa atatatatga catataaatg      1671
tattgtagct ttccggtgtc agccacggtg tatttttcca cttggaatga aattgtatca      1731
actgtgacat tatatgcact agcaataaaa tgctaattgt ttcatgctgt                 1781

<210> SEQ ID NO 9
<211> LENGTH: 4
<212> TYPE: PRT
<213> ORGANISM: Artificial Sequence
<220> FEATURE:
<223> OTHER INFORMATION: Added peptide to derive Human SDF-1-beta

<400> SEQUENCE: 9

Arg Phe Lys Met
1

<210> SEQ ID NO 10
<211> LENGTH: 4
<212> TYPE: PRT
<213> ORGANISM: Artificial Sequence
<220> FEATURE:
<223> OTHER INFORMATION: Added peptide to derive Murine SDF-1-beta

<400> SEQUENCE: 10

Arg Leu Lys Met
1

<210> SEQ ID NO 11
<211> LENGTH: 27
<212> TYPE: DNA
<213> ORGANISM: Artificial Sequence
<220> FEATURE:
<223> OTHER INFORMATION: CXCR4-specific forward primer

<400> SEQUENCE: 11
tagcggccgc gttgccatgg aaccgat                                           27

<210> SEQ ID NO 12
<211> LENGTH: 27
<212> TYPE: DNA
<213> ORGANISM: Artificial Sequence
<220> FEATURE:
<223> OTHER INFORMATION: CXCR4-specific reverse primer

<400> SEQUENCE: 12
gcgtcgactt tgcataaggg ttagctg                                           27
```

INHIBITING VASCULARIZATION USING ANTIBODIES TO CXCR4 AND SDF-1

RELATED APPLICATIONS

This application is a continuation of U.S. application Ser. No. 09/646,785 (filed Feb. 16, 2001) (now abandoned), which is a U.S. National Phase Application of International Application No. PCT/JP99/01448 (filed Mar. 23, 1999), which claims the benefit of Japanese Patent Application No. P1998-095448 (filed Mar. 24, 1998), all of which are incorporated by reference in their entirety.

SEQUENCE LISTING SUBMISSION VIA EFS-WEB

A computer readable text file, entitled "046124-5042-01-SequenceListing.txt" created on or about Jan. 4, 2012 with a file size of about 29 kb contains the sequence listing for this application and is hereby incorporated by reference in its entirety.

TECHNICAL FIELD

This invention relates to a novel vascularization inhibitor, an anti-solid cancer agent, and a therapeutic agent for a disease pathologically caused by neovascularization, each comprising a CXCR4 inhibitor as the effective ingredient. Further, the invention relates to a tissue-repairing agent comprising a CXCR4 potentiator as the effective ingredient.

BACKGROUND ART

In the past, it has been known that when tumor cells invade out of the blood vessels, vascular endothelial cells rupture. It is also known that neovascularization is deeply involved in the proliferation and migration of cancer and that tumor cells produce and release a variety of neovascularization factors. Especially, neovascularization is considered crucial to the proliferation of solid tumors.

Therefore, a substance that inhibits the neovascularization has the potential to be an anticancer agent that is provided with a novel mode of action. For this reason, several types of neovascularization inhibitory substances such as steroids and metabolic products of microorganisms have already been tested for use. ("Manual for Studies on Cancer Invasion and Metastasis," The Cancer Metastasis Society Ed., Kinhodo Publisher, 159-182 (1994)). However, it is strongly desired that novel neovascularization inhibitory substances with the action of more effectively inhibiting the proliferation and metastasis of cancers be discovered.

DISCLOSURE OF THE INVENTION

This invention provides a vascularization inhibitor, an anti-solid cancer agent, or a therapeutic agent for a disease pathologically caused by neovascularization, each comprising an inhibitor of a chemokine receptor with the action of more effectively inhibiting the proliferation, invasion and metastasis of a cancer. Further, an object of the invention is to provide a tissue-repairing agent comprising as the effective ingredient, a potentiator of chemokine receptors.

Specifically, the present inventors pursued extensive research in order to solve the above-identified problems; and as a result, they have discovered that when knockout mice lacking in pre-B-cell growth stimulating factor/stromal-cell derived factor (hereafter referred to as "PBSF/SDF-1" or "SDF-1") which is a CXC chemokine as well as in CXCR4 which is a chemokine receptor are created, the vascularization in the mice is suppressed, and namely, suppression of CXCR4 results in the suppression of vascularization. Such finding means that the chemokine receptor CXCR4 is essential for neovascularization.

Neovascularization of living tissues generally occurs through remodeling of the preexisting vascular system when they grow to perform their specific functions during development. Analyses of the mutant mice have determined that the molecules required by early vascular systems are largely receptor tyrosine kinases and their ligands. (Risau, w. Nature 386, 671-674 (1997); Folkman, J. & D'Amore, P. A. Cell 87, 1158-1155 (1996); and Lindahl, P., et al., science 277, 242-245 (1997)). However, substances responsible for vascularization during organogenesis have not yet been identified, because most of these mice die during early gestation before development of their tissues.

The structure of chemokine receptor CXCR4 according to this invention has already been known. (Bleul, C. C. et al., Nature 382, 829-883 (1996); Oberlin, E. et al., Nature 382, 888-835 (1996); and Nagasawa, T. et al., Proc. Natl. Acad. Sci. USA 93, 14726-14729 (1996)). CXCR4 is a seven-transmembrane-spanning G-protein-coupled protein and a receptor for PBSF/SDF-1 which is a CXC chemokine. The aforementioned factor is thought to be responsible for B-cell lymphopoiesis, bone marrow myelopoiesis and cardiac ventricular septum formation (Nagasawa, T. et al., Nature 382, 685-688 (1996)). CXCR4 also functions as a co-receptor for T-cell-line-tropic HIV-1 (Feng, Y. et al., Science 272, 872-877 (1996)). CXCR4 has further been reported to be expressed in cultured endothelial cells (Volin, M. V. et al., Biochem. Biophys. Res. Commun. 242, 46-53 (1998)).

In addition, the present inventors have discovered that the above-mentioned CXCR4 is expressed in developing vascular endothelial cells, and that mice lacking CXCR4 or its ligand PBSF/SDF-1 show defective formation of the large vessels being supplied to the gastrointestinal tract. Such finding means that the CXCR4 and PBSF/SDF-1 signaling systems are essential for the formation of median arteriovein supplying nutrient to the gastrointestinal tract. Furthermore, the present inventors have found that mice lacking CXCR4 are apt to die in utero just as seen in mice lacking PGSF/SDF-1. Such finding suggests that CXCR4 is the most critical, primary physiological receptor for PBSF/SDF-1.

Based on the foregoing observations by the present inventors, it is contemplated that substances capable of inhibiting the action due to CXCR4 may inhibit vascularization and thus can be effective anticancer agents, since the vascularization is essential for the maintenance and enlargement of cancerous tissues.

It is likewise contemplated that substances capable of inhibiting CXCR4 can be therapeutic agents for the treatment of diseases involving neovascularization.

It is further contemplated that promotion of the action due to CXCR4 accelerates vascularization and thus can be a remedy for a disease where the vascularization is desired.

More specifically, as will be summarized below, this invention provides a vascularization inhibitor, an anti-solid tumor agent, or a therapeutic agent for a disease pathologically caused by neovascularization, each comprising as the effective ingredient, a substance that inhibits the action due to CXCR4. The invention also provides a tissue-repairing agent or the like comprising as the effective ingredient, a substance that potentiates the action due to CXCR4.

That is, this invention provides a vascularization inhibitor comprising a CXCR4 inhibitor as the effective ingredient.

Also, this invention provides an anti-solid cancer agent comprising a CXCR4 inhibitor as the effective ingredient.

Further, this invention provides a therapeutic agent for a disease pathologically caused by neovascularization, comprising a CXCR4 inhibitor as the effective ingredient.

Still further, the invention provides a tissue-repairing agent comprising a CXCR4 potentiator as the effective ingredient.

Because the formation of median or large arterioveins is essential for the maintenance and enlargement of a cancer tissue that exceeds a certain size, the vascularization inhibitor of this invention blocks the CXCR4 or PBSF/SDF-1 signaling system, thus suppressing the maintenance and enlargement of the cancer tissue.

The finding obtained in this invention suggests the possibility that the CXCR4 and PBSF/SDF-1 signaling systems contribute to the universal vascularization. Therefore, in diseases of which a particular kind of cancer or neovascularization is the major pathological cause, it is likely that CXCR4 or PBSF/SDF-1 is deeply involved in the pathological cause; in this case, there is the possibility that these diseases can be suppressed by blocking CXCR4 or PBSF/SDF-1 individually or concurrently with other molecules.

In the present specification and the drawings, the abbreviations for bases or amino acids are those following the IUPAC-IUB Commission on Biochemistry Nomenclature or those based on what is customary in the art. Illustrated below are their examples. Where amino acids are meant and there may be their optical isomers, they represent L-forms unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
G or Gly: glycine
A or Ala: alanine
V or Val: valine
L or Leu: leucine
I or Ile: isoleucine
S or Ser: serine
T or Thr: threonine
C or Cys: cysteine
M or Met: methionine
E or Glu: glutamic acid
D or Asp: aspartic acid
K or Lys: lysine
R or Arg: arginine
H or His: histidine
F or Phe: phenylalanine
Y or Tyr: tyrosine
W or Trp: tryptophan
P or Pro: proline
N or Asn: asparagine
Q or Gln: glutamine
BSA: bovine serum albumin
FBS: fetal bovine serum
PBS: phosphate buffer saline
SDS: sodium dodecyl sulfate

BRIEF DESCRIPTION OF THE DRAWINGS

FIG. 13A is a photograph showing CXCR4 and PBSF/SDF-1 expression in a gastrointestinal tract tissue through in situ hybridization. Serial sections of the wild-type mesentery connecting to the mid-gut loop were stained with haematoxylin and eosin. "m" represents mesentery, "i" intestine, "a" superior mesenteric artery, and "v" superior mesenteric vein.

FIG. 13B is a photograph showing CXCR4 and PBSF/SDF-1 expression in a gastrointestinal tract tissue through in situ hybridization. Hybridization was done with a CXCR4-specific probe. Arrows indicate the stained endothelial cells of the mesenteric vessels.

FIG. 13C is a photograph showing CXCR4 and PBSF/SDF-1 expression in a gastrointestinal tract tissue through in situ hybridization. Hybridization was done with a PBSF/SDF-1-specific probe. PBSF/SDF-1 was expressed in mesenchymal cells surrounding the endothelial cells in the mesentery.

FIG. 13D is a photograph showing CXCR4 and PBSF/SDF-1 expression in the gastrointestinal tract tissue through in situ hybridization. Serial sections of the wild-type mesentery connecting to the mid-gut loop were stained with haematoxylin and eosin. FIG. 13D is an enlargement of blood vessels arising from the superior mesenteric artery shown in FIG. 13A, where strong expression of CXCR4 was observed in the vascular endothelial cells.

FIG. 13E is a photograph showing CXCR4 and PBSF/SDF-1 expression in the gastrointestinal tract tissue through in situ hybridization. Hybridization was done with the CXCR4-specific probe. FIG. 13E is an enlargement of blood vessels arising from the superior mesenteric artery shown in FIG. 13B, where strong expression of CXCR4 was observed in the vascular endothelial cells. Arrow indicates the stained endothelial cells of the mesenteric vessels.

FIG. 13F is a photograph showing CXCR4 and PBSF/SDF-1 expression in a gastrointestinal tract tissue through in situ hybridization. It is a section of an E18.5 wild-type embryonic bone marrow, showing CXCR4 expression in hematopoietic cells but no expression in spindle-shaped stroma cells.

BEST MODE FOR CARRYING OUT THE INVENTION

Figure 1:
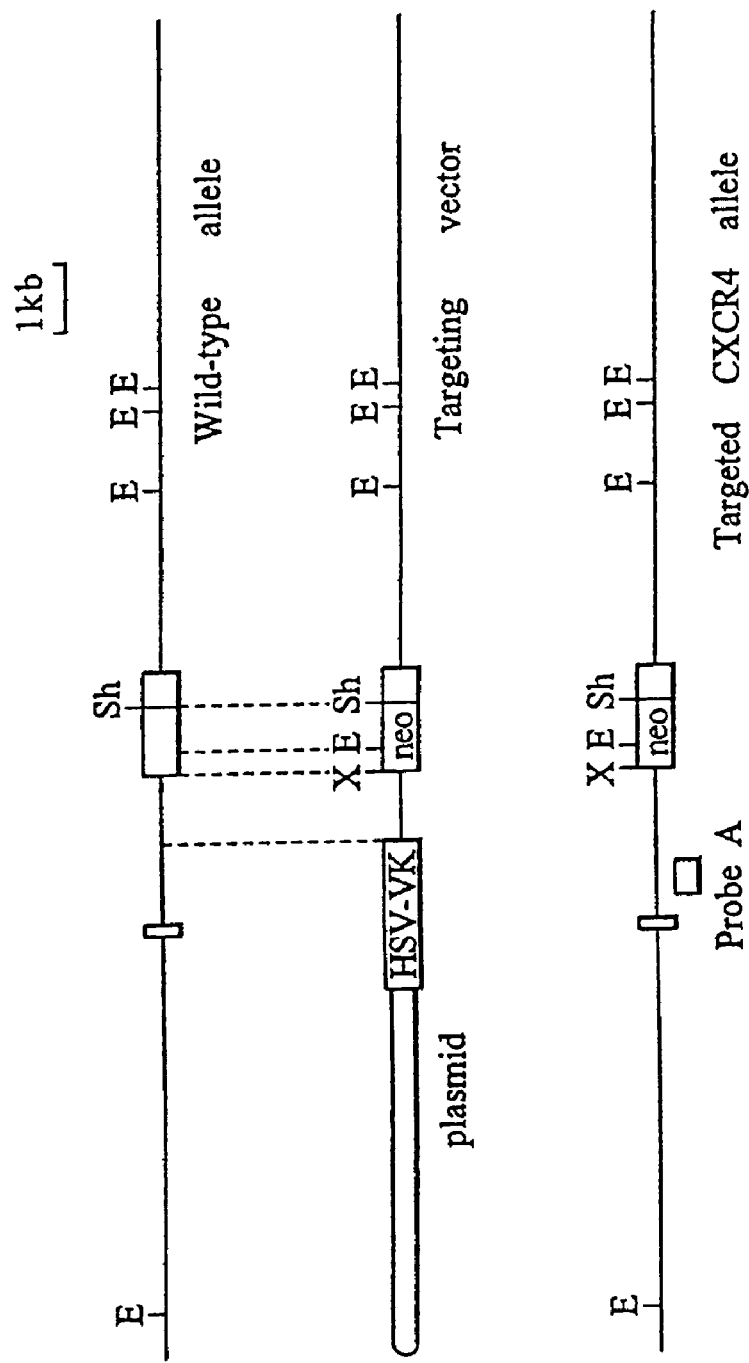
FIG. 1 is a graph showing a targeting strategy for the CXCR4 gene. In the figure, there are shown the CXCR4 wild-type allele at the top, a targeting vector in the middle, and a predicted mutant allele at the bottom. The coding regions of the genes are indicated by black boxes. Empty boxes indicate the 5'- and 3'-untranslated regions. Dotted lines indicate homologous fragments used in the targeting vector. Probe A is an external probe for Southern hybridization. Restriction sites are E (EcoRI), Sh (SphI), and X (XhoI), respectively.

The vascularization inhibitor, the anti-solid cancer agent, or the therapeutic agent for a disease pathologically caused by neovascularization according to this invention comprises as the effective ingredient, a substance that inhibits the action of CXCR4 which is a chemokine receptor. On the other hand, the tissue-repairing agent according to the invention comprises as the effective ingredient, a substance that potentiates the action of CXCR4.

The amino acid sequence of CXCR4 has already been known. Specifically, the amino acid sequence of human CXCR4 and the amino acid sequence of murine CXCR4 are set forth in SEQ ID NOs: 1 and 3, respectively. The base sequence of human CXCR4 and the base sequence of murine CXCR4 are set forth in SEQ ID NO: 2 (base positions 1-1056) and SEQ ID NO: 4 (base positions 1-1077), respectively.

Also, the amino kid sequence of SDF-1, which is a ligand binding to CXCR4, has already been known. There are two types of SDF-1 differing in the length of amino acid sequence, i.e., SDF-1-α and SDF-1-β. Specifically, the amino acid sequence of human SDF-1-α is set forth in SEQ ID NO: 5 and its base sequence in SEQ ID NO: 6 (base positions 474-740). Human SDF-1-β is derived froth human SDF-1-α by appending four amino acid residues, Arg Phe Lys Met (SEQ ID NO: 9), to a C-terminus thereof.

The amino acid sequence of murine SDF-1-α is set forth in SEQ ID NO: 7 and its base sequence in SEQ ID NO: 8 (base positions 82-348). Murine SDF-1-β is derived from murine SDF-1-α by appending four amino acid residues, Arg Leu Lys Met (SEQ ID No: 10), to a C-terminus thereof. For human and murine SDF-1's, the sequence of from the 1st amino acid (Met) to the 21st amino acid (Gly) is a signal sequence.

CXC chemokines that have hitherto been known include, in addition to PBSF/SDF-1 mentioned above, IL-8 (Yoshimura., T. et al., Proc. Natl. Acad. Sci. U.S.A., 84, 9233-9237 (1987)), NAP-2 (Walz. A., et al., Biochem. Biophys. Res. Comun., 159, 969-975 (1989)), NAP-4, GRO α (Richmondo, A. et al., J. Cell. Biochem., 36, 185-198 (1988)), GRO β (Haskill, S. et al., Proc. Natl. Acad. Sci. U.S.A., 87, 77732-7736 (1990)), GRO γ (Haskill, S. et al., ibid. (1990)), GCP-2 (Proost, P. et al., J. Immunol., 150, 1000-1010 (1993)), ENA-78 (Wayz, A. et al., J. Exp. Med., 174, 1355-1362 (1991)), PF-4 (Deuel, T. F. et al., Proc. Natl. Acad. Sci. U.S.A. 74, 2256-2258 (1977)), and IP-10 (Dewald, B. et al., Immunol. Lett., 32, 81-84 (1992)).

There are no particular limitations to substances that inhibit the action due to CXCR4 that can be used in this invention; and they may be substances that inhibit the action due to CXCR4 with the result of inhibition of neovascularization.

Specifically mentioned are: (1) a substance based on inhibition of the binding itself between the ligand (SDF-1) and the receptor (CXCR4); (2) a substance based on inhibition of the signaling from CXCR4 to nuclei; (3) a substance that inhibits the expression of CXCR4 itself; and (4) a substance that inhibits the expression of SDF-1 itself.

(1) For the substance that inhibits the binding itself between SDF-1 and CXCR4, there are a substance that inhibits SDF-1 and a substance that inhibits CXCR4.

More specifically, the substance that inhibits SDF-1 is classified into a substance that inhibits CXCR4 in antagonistic competition with SDF-1 and a substance that inhibits SDF-1 from binding to CXCR4 by binding to SDF-1. For the substance that inhibits CXCR4 in antagonistic competition with SDF-1, there are concretely mentioned a protein having a SDF-1-like structure, a fused protein of the foregoing protein with another peptide or polypeptide, a low molecular weight compound having a structure similar to a partial peptide of SDF-1 or a binding site of SDF-1, and the like.

For the substance that inhibits SDF-1 from binding to CXCR4 by binding to SDF-1, there are concretely mentioned an anti-SDF-1 antibody, a fragment thereof having possessing binding activity, a fused protein possessing binding activity to SDF-1, a substance that induces a structural change in SDF-1, a low molecular weight compound that binds to the CXCR4-binding site of SDF-1, and the like.

More specifically, the substance that inhibits CXCR4 is classified into a substance that inhibits CXCR4 in antagonistic competition with CXCR4 for binding to SDF-1 and a substance that inhibits SDF-1 from binding to CXCR4 by binding to CXCR4. For the substance that inhibits CXCR4 in antagonistic competition with CXCR4 for binding to SDF-1, there are concretely mentioned a soluble CXCR4 that antagonizes CXCR4 in inhibition, a protein having a CXCR4-like structure, a fused protein of the foregoing protein with another peptide or polypeptide, a low molecular weight compound having a structure similar to a partial peptide of CXCR4 or a binding site of CXCR4, and the like.

For the substance that inhibits SDF-1 from binding to CXCR4 by binding to CXCR4, there are concretely mentioned an anti-CXCR4 antibody, a fragment thereof possessing its binding activity, a fused protein possessing binding activity to CXCR4, a substance that induces a structural change in SDF-1, a low molecular weight compound that binds to the SDF-1-binding site, and the like.

Examples of the substance that inhibits the binding itself between CXCR4 and SDF-1 include T22 (T. Murakami, et al., J. Exp. Med., 186, 1389-1393 (1997)), ALX40-4C (J. Exp. Med., 186, 1395-1400 (1997)), AMD3100 (J. Exp. Med., 186, 1383-1388 (1997); Nat. Med., 4, 72-77 (1998)), and the like. As to the methods for preparation of these substances, they can, for example, be done by the method as described in J. Exp. Med., 186, 1189-1191 (1997) with any possible modifications.

(2) There is no particular limitation to the substance based on inhibition of the signaling from CXCR4 to nuclei insofar as it is a substance having such action. For the substance based on inhibition of the signaling from CXCR4 to nuclei, there are mentioned inhibitors of the signaling system existing downstream of a G protein-coupled protein, such as an MAK cascade inhibitor, a phospholipase C (PLC) inhibitor and a kinase inhibitor for PI3 kinase.

(3) For the substance that inhibits the expression of CXCR4 itself, there are mentioned a substance that apparently makes CXCR4 disappear on cells and a substance that inhibits the expression of CXCR4 itself. A specific example of the substance that apparently makes CXCR4 disappear on cells is a substance that induces down-regulation of CXCR4. The "induction of down-regulation of CXCR4" specifically means such a function that it acts on the cell membrane to alter mobility thereof and thereby to make CXCR4 disappear from the cell membrane. For example, dexamethasone is mentioned as a substance possessing the function.

For the substance that inhibits the expression of CXCR4 itself, there are concretely mentioned an antigene, an antisense (antisense oligonucleotide and antisense RNA expressed by antisense vector), a ribozyme, and a substance that inhibit the expression control site of CXCR4 such as a promoter or an enhancer.

From the examples which will be described later, it has become evident that when a vector containing a part of the CXCR4 gene is used to cause the deficiency of CXCR4, vascularization is suppressed. Therefore, the inhibition of CXCR4 by the antigene, antisense, or ribozyme of CXCR4 will suppress vascularization.

Antisense oligonucleotides that can preferably be used in this invention include CXCR4 genes, SDF-1 genes against CXCR4, nucleotides (DNAs or RNAs) selectively hybridizable to the genes of substances that are involved in the signaling system based on CXCR4, and derivatives thereof (such as antisense oligonucleotides). This invention, for example, encompasses antisense oligonucleotides that hybridize to any site of the base sequence of human CXCR4 gene as set forth in SEQ ID NO: 2.

Preferably, the antisense oligonucleotide is an antisense oligonucleotide to at least 20 consecutive nucleotides within the base sequence set forth in SEQ ID NO: 2. More preferably, the antisense oligonucleotide is the at least 20 consecutive nucleotides containing a translation initiation codon.

As used herein, "antisense oligonuclotide" is not only one having nucleotides that correspond to the nucleotides constituting the predetermined region of DNA or RNA and that are all complementary thereto, but also may allow one or more mismatches of nucleotide to be present therein insofar as the oligonuclotide and the DNA or the RNA are able to selectively and stably hybridize to the base sequence set forth in SEQ ID NO: 2. By "selectively and stably hybridize" is meant those having at least 70%, preferably at least 80%, more preferably at least 90%, most preferably 95% or greater homology of base sequence in the nucleotide sequence region of at least 20, and preferably 30 consecutive nucleotides. In the present specification, "homology" indicates "identity."

When the oligonucleotide derivative used in this invention is a deoxyribonucleotide, the structure of each derivative is represented by formula 1:

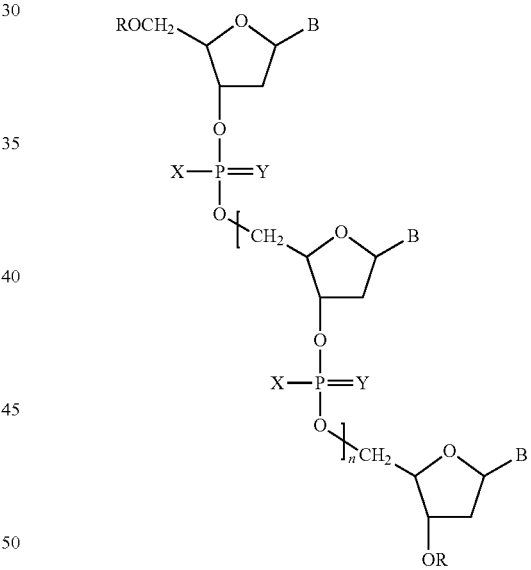

In the formula, X may independently be any of oxygen (O), sulfur (S), a lower alkyl group, a primary amine and a secondary amine. Y may independently be either oxygen (O) or sulfur (S). B is selected from adenine, guanine, thymine, or cytosine, and is principally an oligonucelotide complementary to DNA or RNA of the human CXCR4 gene. R is independently hydrogen (H), a dimethoxytrytyl group or a lower alkyl group. n is from 7 to 28.

Preferable oligonucleotide derivatives are not limited to oligonucleotides that have not been modified, but may be modified oligonucleotides, as will be illustrated below. These modified forms include lower alkyl phosphonate derivatives of such types as methyl phosphonate or ethyl phosphonate, phosphorothioate derivatives, phosphoroamidates, and the like.

EXAMPLES OF: 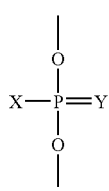

METHYL PHOSPHONATE: 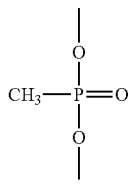

PHOSPHOROTHIOATE: 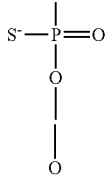

PHOSPHORODITHIOATE: 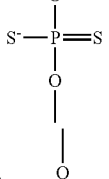

PHOSPHOROAMIDATE: 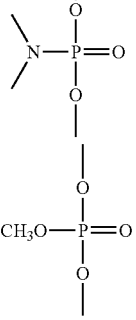

PHOSPHORIC TRIESTER: 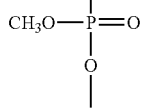

These oligonucleotide derivatives can be obtained by standard methods as described below. The oligonucleotides of formula (1) wherein X and Y are both O may readily be prepared with a commercial DNA synthesizer such as one available from Applied Biosystems; for their preparation method, solid phase synthesis employing phosphoroamidites, solid phase synthesis employing hydrogen phosphonates and the like can be used to obtain them.

The phosphoric triester modified forms wherein X is a lower alkoxy group can be obtained by standard methods: for example, oligonucleotides obtained by chemical synthesis are treated with a DMF/methanol/2,6-lutidine solution of tosyl chloride. The alkyl phosphonate modified forms wherein X is an alkyl group can be obtained according standard methods, for example, by using phosphoamidites. The phosphorothioate modified forms wherein X is S can be obtained according standard methods, for example, by solid phase synthesis using sulfur, or alternatively by solid phase synthesis using tetraethyl thiuram disulfide. The phosphorodithioate modified forms wherein X and Y are both S can be obtained according to solid phase synthesis, for example, by converting bisamidites into thioamidites and allowing sulfur to act on the thioamidites. The phosphoroamidate modified forms wherein X is a primary or secondary amine can be obtained according to solid phase synthesis, for example, by treating hydrogenphosphonates with a primary or secondary amine; alternatively, they can be obtained by oxidizing amidites with tert-butyl hydrogen peroxide.

Purification and the assurance of purity may be carried out by high speed liquid chromatography or polyacrylamide gel electrophoresis. The confirmation of molecular weights may be carried out by electrospray ionization mass spectrometry or fast atom bombardment-mass spectrometry.

The antisense oligonucleotide derivatives used in this invention act on a CXCR4 receptor or a ligand thereof, as well as on cells producing a signaling substance based on CXCR4, and bind to DNA or RNA encoding the peptide, thereby inhibiting its transcription or translation, or promoting the decomposition of mRNA; as a result, they possess an inhibitory effect on the action due to CXCR4 by suppressing the expression of the peptide.

Consequently, the antisense oligonucleotides used in this invention have utility in inhibiting neovascularization. Neovascularization inhibitors comprising the antisense oligonucleotides of this invention are useful as therapeutic agents for cancers, particularly solid cancers.

Preparation of CXCR4 antisense vectors may follow the methods that are commonly used. Specifically, cDNA encoding CXCR4 is linked to an AAV vector (adeno-associated virus vector), MLV vector (murine leukemic virus vector), HIV vector, or the like in the antisense direction. By "antisense direction" is meant linking to the 3'-side of the cDNA to be introduced in the downstream of the promoter. The antisense RNAs synthesized from cDNAs contained in these vectors constitutively suppress the expression of CXCR4 in hosts.

Antisense DNAs or RNAs can be introduced into cells by using means such as the liposome method, the HVJ liposome method, or the positively charged liposome method. The introduction of a CXCR4 antisense DNA or RNA allows for the constitutive inhibition of expression of CXCR4.

(4) For the substance that inhibits the expression of SDF-1 itself against CXCR4, there are mentioned an antisense substance that inhibits the expression of SDF-1 and a substance that inhibits the expression control site such as a promoter.

The antibodies described above that can be used in this invention, such as anti-SDF-1 antibodies and anti-CXCR4 antibodies can be prepared as polyclonal or monoclonal antibodies using techniques that are known in the art. Especially, monoclonal antibodies derived from mammals are preferred as the antibodies that are used in the invention. The monoclonal antibodies derived from mammals include those produced by hybridomas and those produced by the hosts that have been transformed with expression vectors containing antibody genes by techniques in genetic engineering. These antibodies are those which possess the above-mentioned properties.

Antibody-producing hybridomas can principally be prepared using techniques known in the art in the following manner. That is, a desired antigen is used as the sensitizing antigen to carry out immunization according to a conventional immunization method; and the resulting immunized cells are fused with parent cells known in the art by a conventional cell fusion method, and monoclonal antibody-producing cells are subjected to cloning by a conventional cloning method.

The mammals to be immunized with the sensitizing antigen are not particularly limited, but should preferably be selected in consideration of their compatibility with the parent cells to be used in the cell fusion. Generally, animals belonging to the rodent family, such as mouse, rat and hamster are used. Immunization of animals with the sensitizing antigen is carried out by a method known in the art.

For the mammalian myeloma cells used as the other parent cells for fusion with the immunocytes, a variety of cell lines already known in the art may appropriately be employed. The cell fusion between the immunocytes and myeloma cells may be carried out basically according to a conventional method, such as the method of Milstein et al (Kohler, G. and Milstein, C., Methods Enzymol., 73, 3-46 (1981)) with any possible modifications.

The obtained hybridomas are selected by culturing in a common selection medium, such as HAT medium (medium containing hypoxanthine, aminopterin and thymidine). Culturing in the HAT medium is continued for a sufficient time to allow killing of all the cells other than the targeted hybridomas (the non-fused cells), which is usually from a few days to a few weeks. The usual limiting dilution method is then performed for screening and cloning of hybridomas producing the target antibodies. Antibodies may be acquired from the thus-obtained hybridomas following a method that is commonly employed.

In addition to acquisition of the hybridomas by immunizing an animal other than human with the antigen as described above, human lymphocytes are sensitized in vitro with a desired antigen protein or antigen-expressing cell, and the sensitized B lymphocytes are fused with human myeloma cells, such as U266, whereby desired humanized antibodies possessing the binding activity toward the desired antigen or antigen-expressing cell may be obtained. Furthermore, the desired humanized antibodies may be acquired according to the aforementioned method by administering the antigen or the antigen-expressing cell to a transgenic animal having a reparatory of human antibody genes.

An antigen gene is cloned as a monoclonal antibody from the hybridoma and incorporated into a suitable vector; and this is introduced into a host, and the gene manipulation technology is used to produce a recombinant antibody, which may then be used in this invention. See, for example, Carl, A. K. Borrenbaeck, James, W. Larrick, Therapeutic Monoclonal Antibodies, published in the United Kingdom by Macmillan Publishers Ltd. 1990.

In this invention, recombinant antibodies that have been artificially modified for the purpose of lowering heterogeneous antigenicity against humans, such as chimeric antibodies (European Patent Publication EP125023) and humanized antibodies (European Patent Publication EP125023), may be used. These antibodies can be produced by known methods.

The chimeric antibody comprises the variable region of an antibody derived from a mammal other than human and the constant region (C region) derived from a human antibody. The humanized antibody comprises a complementarity-determining region of an antibody derived from a mammal other than human, a framework region (FR) derived from a human antibody and a C region. They are useful as the effective ingredients in this invention because of diminished antigenicity in the human body.

The antibodies used in this invention may be fragments of antibody or modified substances thereof insofar as they can desirably be used in the invention. The fragments of antibody, for example, include Fab, F(ab')$_2$, Fv, and single chain Fv (scFv) obtainable by linking Fv from H chain and Fv from L chain via a suitable linker. Specifically, an antibody is treated with an enzyme such as papain or pepsin to produce antibody fragments. Alternatively, genes encoding these antibody fragemnets are constructed and are introduced into an expression vector, after which they are expressed in suitable host cells.

The phage library method can be utilized to obtain the antibodies that are used in this invention. (Marks, C. et al., The New England Journal Medicine 335, 730-733). For example, a cDNA library is acquired from human B cells that comprises a human antibody V region, such as the gene encoding scFv. This cDNA library is introduced into a phage vector such as the M13 phage surface presenting vector, and this is allowed to infect *E. coli*. The cDNA library is expressed in *E. coli*, and the antibody V region is produced on the cell surfaces. If selection is made on a plate coated with the desired antigen based on antigen-binding activity, a gene encoding the desired antibody can be obtained.

Antibodies possessing stronger binding activity to antigens may be obtained by the chain shuffling method with application of the phage library method. (Akamatsu, Y. and Tsurushita, N. Medical Immunology 27, 273-286 (1994)). Specifically, one member of the V region of an antibody gene that has been separated (such as VH) is fixed; and a new library is constructed from the mixture of the one member and the other member prepared from B cells (such as VL). Clones that bind to the antigen more strongly than do the others may be separated from the library.

It is also possible to obtain antibodies possessing stronger binding activity to antigens by introducing artificial mutations into the amino acid sequences of the antibodies. (Akamatsu, Y. and Tsurushita, N. Medical Immunology 27, 273-286 (1994)). More specifically, the mutation is introduced into a gene encoding the cloned antibody V region, and this gene is expressed by the phage library method described above. Thereby, it becomes possible to obtain a gene encoding the antibody that possesses stronger binding activity to antigen.

These fragments of antibody can be produced by hosts after their genes are acquired and expressed in the same manner as described previously above. As used in the present specification, "antibody" encompasses these fragemnts of antibody.

Modified forms of antibody can employ antibodies that are bound to various molecules such as polyethylene glycol (PEG). As used in the present specification, the "antibody" encompasses these modified forms of antibody. Acquisition of these modified forms of antibody can be done by subjecting the obtained antibodies to chemical modification. These methods have already been established in the art.

The antibodies that are expressed and produced as described above can be separated from the host cells intracellularly or extracellularly, and can be purified to homogeneity according to methods that are commonly used. Concentration measurement can be carried out by the measurement of absorbance, ELISA or the like.

For the CXCR4 inhibitor used in this invention, there is mentioned a protein having an SDF-1- or CXCR4-like structure (structure-resembling protein). This substance is one that possesses binding activity to SDF-1 or CXCR4 and that does not transmit its biological activity. That is, it blocks signaling by SDF-1, because it binds to CXCR4 in a competitive manner with SDF-1, but does not transmit the biological activity of SDF-1.

SDF-1 structure-resembling proteins may be prepared by introducing mutations into the amino acid sequence of SDF-1 through substitution of amino acid residues thereof. For SDF-1 on which the SDF-1 structure-resembling proteins are based, its source does not matter; however, it is preferably human SDF-1 in consideration of its antigenicity or the like. Specifically, the amino acid sequence of SDF-1 is used to predict its secondary structure by using a molecular modeling program known in the art such as WHATIF (Vriend et al., J.

Mol. Graphics 8, 52-56 (1990)); and further the influence on the whole, of the amino acid residue to be substituted is evaluated to carry out the preparation.

After a suitable amino acid residue to be substituted has been determined, a vector containing the base sequence that encodes human SDF-1 gene is used as a template, and the introduction of mutation is carried out by the PCR method (polymerase chain reaction), which is commonly done, so that the amino acid may be substituted. This allows a gene encoding the SDF-1 structure-resembling protein to be obtained. This gene is incorporated into a suitable expression vector as appropriate, and the SDF-1 structure-resembling protein can be obtained according to the methods for the expression, production and purification of the recombinant antibodies as described previously. SDF-1 of which the N-terminus has been deleted is known as an SDF-1 structure-resembling protein (EMBO J. 16, 6996-7007 (1997)).

The SDF-1 partial peptide or the CXCR4 partial peptide that is used in this invention is a substance that possesses binding activity to CXCR4 or to SDF-1 and that does not transmit the biological activity of SDF-1. That is, the SDF-1 partial peptide or the CXCR4 partial peptide specifically inhibits SDF-1 from binding to CXCR4, because each binds to CXCR4 or to SDF-1 and traps either of them.

Consequently, they block signaling by SDF-1, because they do not transmit the biological activity of SDF-1.

The SDF-1 partial peptide or the CXCR4 partial peptide is a peptide comprising a part or the whole of the amino acid sequence of the region, which is responsible for the binding between SDF-1 and CXCR4, in the amino acid sequence of SDF-1 or of CXCR4. Such a peptide usually comprises 10-80 amino acid residues, preferably 20-50 amino acid residues, and more preferably 20-40 amino acid residues.

The SDF-1 partial peptide or the CXCR4 partial peptide can be prepared by identifying in the amino acid sequence of SDF-1 or of CXCR4, the region that is responsible for the binding between SDF-1 and CXCR4 and by preparing a part or the whole of the amino acid sequence of said region according to a method that is commonly known, such as a technique in genetic engineering or peptide synthesis.

To prepare the SDF-1 partial peptide or the CXCR4 partial peptide by the technique in genetic engineering, a DNA sequence encoding the desired peptide is incorporated into an expression vector, and the methods for expression, production and purification of the recombinant antibodies as described previously are followed with any possible modifications, thus enabling the preparation.

To prepare the SDF-1 partial peptide or the CXCR4 partial peptide by peptide synthesis, methods that are commonly used in the peptide synthesis, such as the solid phase synthesis or the liquid phase synthesis, can be employed. Concretely, the method as described in "Development of Drugs, Peptide Synthesis Vol. 14, Ed. by Nariaki Yajima, Hirokawa Publisher (1991) may be followed with any possible modifications. For the solid phase synthesis, the following method is, for example, employed: an amino acid corresponding to the C-terminus of the peptide to be synthesized is allowed to bind to a support insoluble in an organic solvent; and the reaction wherein an amino acid protected with suitable protecting groups at its α-amino group and side-chain functional group is condensed to the foregoing amino acid one amino acid at a time in the direction of from the C-terminus to the N-terminus and the reaction for detaching the protecting group for the α-amino group of the amino acid or peptide bound to the resin are alternately repeated to elongate the peptide chain. The solid phase peptide synthesis is largely classified into the Boc method and the Fmoc method, depending on the kind of protecting groups to be used.

After the objective peptide is synthesized in this manner, deprotection reaction is done and the peptide is cleaved from the Support for the peptide chain. In the cleavage reaction from the peptide chain, the Boc method can usually employ hydrogen fluoride or trifluoromethanesulfonic acid and the Fmoc method can usually employ TFA. In the Boc method, the protected peptide resin mentioned above is, for example, treated in hydrogen fluoride in the presence of anisole. Subsequently, deprotection of the protecting group and cleavage from the support recovers the peptide.

The product is lyophilized to yield a crude peptide. In the Fmoc method, deprotection reaction and cleavage reaction from the support for the peptide chain can also be carried out in TFA using manipulations similar to those mentioned above.

The resulting crude peptide can be separated and purified by being applied on HPLC. The elution may then be carried out under optimum conditions with a solvent of the water-acetonitrile system that is usually used to purify proteins. The fractions corresponding to the peaks of the obtained profile of chromatography are fractionally separated and lyophilized. The peptide fractions thus purified are identified by molecular weight analysis through mass spectrometry, amino acid composition analysis, amino acid sequencing, or the like.

For the SDF-1 partial peptide or the CXCR4 partial peptide that is used in this invention, its sequence does not matter insofar as each binds to CXCR4 or to SDF-1 and possess no signaling activity. The amino acid sequences that are already known can be used both for the SDF-1 partial peptide and the CXCR4 partial peptide. For example, when the ligand is SDF-1, the amino acid sequences set forth in SEQ ID NO: 5 (human) and SEQ ID NO: 7 (mouse) are usable.

There is no particular limitation to the substance that potentiates the action due to CXCR4 that can be used in this invention. For the substance that potentiates SDF-1, there are mentioned SDF-1 itself, an agonist of SDF-1, and a potentiator of SDF-1 expression. Furthermore, for the substance that potentiates a CXCR4 receptor, there are mentioned CXCR4 itself, an agonist of CXCR4, and a potentiator of CXCR4 expression.

As explained above, use of the vascularization inhibitor according to this invention comprising the CXCR4 inhibitor as the effective ingredient allows for the inhibition of vascularization; therefore, it will exert an antitumor effect (inhibition of neovascularization) on solid cancer in addition to antitumor effects on angiosarcoma (cancer of blood vessels themselves) and Kaposi's sarcoma. It will also exert therapeutic effects against diseases pathologically caused by neovascularization, such as chronic articular rheumatism, psoriasis, and diabetic retinopathy.

If the therapeutic agent for a disease pathologically caused by neovascularization which comprises the substance that potentiates the action of CXCR4 is used, it will be possible to promote neovascularization. The use will exert therapeutic effects on myocardial infarction and diseases involving neovascularization after surgery, such as wound healing, repairing and remodeling of bones, repairing of cartilage, growth of hair, myocardial infarction, brain infarction, and brain trauma.

For the neovascularization inhibition and promotion test methods that can be used in this invention, a neovascularization assay may be employed. There is no particular limitation to this assay, and a method that is commonly known can preferably be used. ("Research Manual for the Invasion and Metastasis of Cancers" the Cancer Metastasis Study Group Ed., Kinhodo, 159-182, (1994)). Specifically, among others, there are mentioned (I) the method for measuring cleavage of the spaces between vascular endothelial cells (i.e., effect on the vascular endothelial cells) which is based on the finding that the vascular endothelial cells rupture when tumor cells invade out of the blood vessels (from the permeability of FITC-dextran); (II) the cornea method known as an in vivo measurement method for identifying a candidate factor that exerts the function of a neovascularization-inducing factor in vivo; (IV) CAM method (chickembryochorioallantoic membrane); (V) the dorsal subcutanea method for measuring the quantity of induced blood vessel by the naked eyes; and (VI) the method for determining the formation of lumen by vascular endothelial cells.

To confirm the antitumor effect, there may be mentioned in vivo experiments using a transplant model or transplant metastasis model and in vitro experiments with cancer cells. Specifically, the method described in "Research Manual for the Invasion and Metastasis of Cancers" the Cancer Metastasis Study Group Ed., Kinhodo, 7-158 (1994) may be used.

The vascularization inhibitor, anti-sold cancer agent, therapeutic agent, tissue-repairing agent, or the like according to this invention may be systemically (by oral route) or locally administered. For example, intravenous injection (such as intravenous drip infusion), intramuscular injection, intraperitoneal injection, or subcutaneous injection may be selected: an appropriate method of administration may be selected depending on the age or the severity of the subject.

The effective unit dose is chosen within the range of from 0.09 mg to 100 mg per kg of body weight. Alternatively, a dose of 1-1000 mg, preferably a dose of 5-50 mg for the subject may be chosen.

The vascularization inhibitor, anti-sold cancer agent, therapeutic agent, tissue-repairing agent, or the like according to this invention may together contain pharmaceutically acceptable carriers or additives, depending on the route of administration. Examples of such carriers and additives include water, organic solvents that are pharmaceutically acceptable, collagen, poly(vinyl alcohol), poly(vinylpyrrolidone), carboxyvinylpolymer, sodium carboxymethyl cellulose, sodium polyacrylate, sodium arginate, water-soluble dextran, sodium carboxymethyl starch, pectin, methylcellulose, xanthan gum, gum arabic, casein, gelatin, agar, diglycerin, propylene glycol, poly(ethylene glycol), vaseline, paraffin, stearyl alcohol, stearic acid, human serum albumin (HSA), mannitol, sorbitol, lactose, surfactants that are accepted as drug additives, etc.

The additives to be used may appropriately (or in combination) be selected among those mentioned above depending on the dosage form, but are not limited thereto.

This invention will be hereinbelow illustrated in greater details by way of examples; however, the invention is in no way limited by those examples.

EXAMPLES

Creation and Analysis of Mice Completely Lacking CXCR4

Genome DNA containing the CXCR4 locus was isolated from a murine cell line 129DNA library (STRATAGENE).

A 1.1-kb genomic fragment containing the 5'-coding region of exon 2 was replaced by the neomycin resistant gene, and the herpes simplex thymidine kinase gene was linked to the 5'-terminus.

The targeting vector was introduced into the cells on day 14.1 of embryogenesis (referred to as "E14.1" hereafter) by electroporation, and a homologous recombination was selected by the use of G418 and ganciclovir and identified by PCR.

The structure of the mutant locus and the presence of a single insert in the ES cell colony were confirmed by Southern hybridization. According to the method as described in Nagasawa, T. et al., Nature 382, 685-688 (1996), the mutant ES cell colony was used to create a mutant mouse by the injection of undifferentiated embryonic cells.

For Southern hybridization, tail DNA was digested with EcoRI, transferred to a nylon membrane, and hybridized to 550-bp probe A with the 5'-homology region.

RT-PCR was performed for 40 cycles, using 3 μg of total RNA isolated from the fetal liver of E18.5 embryos as a starting material according to the standard method. A 630-bp PCR product was amplified using CXCR4-specific primers, i.e., forward primer (SEQ ID NO: 11) and reverse primer (SEQ ID NO: 12). Histological analysis and flow cytometry analysis were carried out substantially according to the method as described in Nagasawa, T. et al., Nature 382, 685-688 (1996).

Immunohistostaining substantially followed the method of Adachi, S., Yoshida, H., Kataoka, H. Nishikawa, S.-I. Int. Immunol. 9, 507-514. The sections of embryos and organs were fixed with 4% paraformaldehyde, dehydrated with methanol, decolorized with 30% hydrogen peroxide in methanol, and hydrated again.

After incubating in PBSMT (PBS containing 1% skim milk powder and 0.3% v/v TritonX-100), the sample was incubated with diluted anti-PECAM antibody (1:250) (PharMingen) in PBSMT at 4° C. overnight. Then, the sample was washed with PBSMT, and incubated with diluted horseradish peroxidase labeled anti-rat Ig antibody (1:500)(Biosource) in PBST at 4° C. overnight.

Subsequently, the sample was thoroughly washed. The embryo was incubated in PBS containing 250 μg/ml diaminobenzidine (Dojin Chemicals) and 0.08% $NiCl_2$ for 30 min. Hydrogen peroxide was added to the sample to provide a final concentration of 0.01%, after which peroxidase staining was carried out. The reaction was quenched after about 30 min.

According to the method as described in Nagasawa, T. et al., Nature 382, 685-688 (1996), a fragment of murine CXCR4 or PBSF/SDF-1 cDNA was used as a probe to carry out antisense transcription.

Mice lacking CXCR4 were created to determine the physiological function of CXCR4. Specifically, a targeting vector was constructed, such that most of exon 2 within the CXCR4 gene which contained all transmembrane-spanning regions critical to the receptor function had been deleted and the deleted portion would be replaced by the neomycin resistant gene (neo). This would result in that after homologous recombination, the complete CXCR4 gene would be substantially deleted.

FIG. 1 is a graph showing a targeting strategy for the CXCR4 gene (denoted as top, middle, and bottom). There are shown the CXCR4 wild-type allele at the top, a targeting vector in the middle, and a predicted mutant allele at the bottom. The coding regions of the genes are indicated by black boxes. Empty boxes indicate the 5'- and 3'-untranslated regions. Dotted lines indicate homologous fragments used in the targeting vector. Probe A is an external probe for Southern hybridization. Here, restriction sites are E (EcORI), Sh (SphI), and X (XhoI), respectively.

Figure 2A:
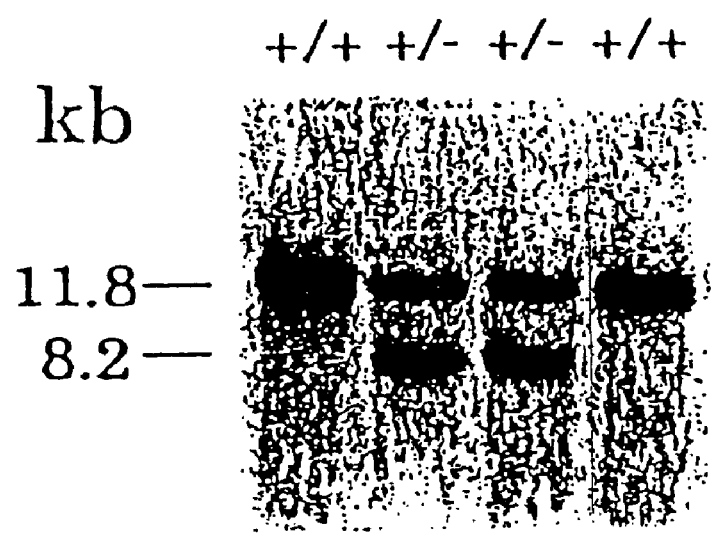
FIG. 2A is a photograph showing the Southern blot analysis of tail DNAs from wild-type (+/+) and heterozygous mutant (+/−) mice. The EcoRI-EcoRI fragments from the 11.8-kb wild-type and the 8.2-kb targeted allele which were identified by probe A are shown in the figure.
Figure 2B:
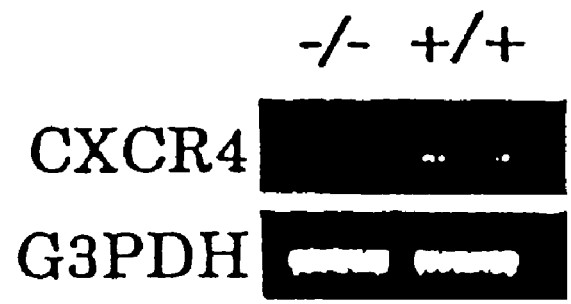
FIG. 2B is a photograph showing the RT-PCR amplification analysis of CXCR4 expression. Total RNAs were prepared from E18.5 wild-type and homozygous mutant embryos, and amplified with CXCR4-specific primers. The RT-PCR amplification employed G3PDH mRNA, which was universally expressed, as a control for the presence of any amplifiable RNA.

FIG. 2A is a photograph showing the Southern blot analysis of tail DNAs from wild-type (+/+) and heterozygous mutant (+/−) mice. The EcoRI-EcoRI fragments from the 11.8-kb wild-type and the 8.2-kb targeted allele which were identified by probe A are shown in the figure. FIG. 2B is a photograph showing the RT-PCR amplification analysis of CXCR4 expression. Total RNAs were prepared from E18.5 wild-type and homozygous mutant embryos, and amplified with CXCR4-specific primers. The RT-PCR amplification employed G3PDH mRNA, which was universally expressed, as a control for the presence of any amplifiable RNA.

Mice with a CXCR4$^{+/-}$ heterozygous mutation were created. The mice were healthy and fertile. CXCR4$^{-/-}$ homozygous mutant embryos were present at the expected ratios until E15.5 of embryogenesis. However, about half of the CXCR4$^{-/-}$ embryos were dead at E18.5 and CXCR4$^{-/-}$ neonates died within an hour similarly to mice lacking PBSF/SDF-1 as previously reported (Nagasawa, T. et al., Nature 382, 685-688 (1996)).

To elucidate the functions of CXCR4 during embryogenesis, expression of CXCR4 in developing embryos was examined by in situ hybridization. High levels of CXCR4 transcripts were detected in the endothelium of developing blood vessels during embryogenesis.

Based on this finding, the effect of CXCR4 gene deficiency on vascularization was investigated. On visual inspection, vitellin and umbilical vessels were normal. Histological examination of E18.5 CXCR4$^{-/-}$ embryos demonstrated the presence of the major blood vessels, including aorta, vena cava, carotid artery, jugular vein, coeliac artery and superior mesenteric artery and superior mesenteric vein. To visualize the vascular system of organs, whole-mount preparations of wild-type and mutant embryos were then immunostained with an anti-PECAM-1 antibody. It is known that PECAM-1 is specifically and stably expressed in all endothelial cells during embryonic period. (Vecchi, A. et al. Eur. J. cell Biol. 63, 247-255 (1994); Baldwin, H. S. et al., Development 120, 2539-2558 (1994)).

Figure 3:
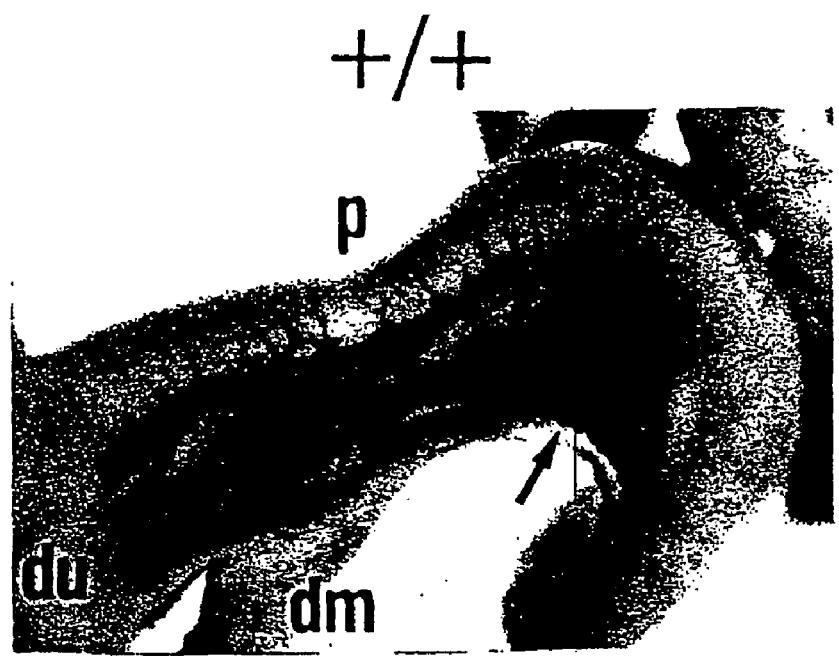
FIG. 3 is a photograph showing defects of gastrointestinal blood vessels at the mesentery and mid-gut loop region in a wild-type CXCR4$^{-/-}$ embryo at E13.5, resulting from immunohistostaining of the mesentery and intestine with anti-PECAM-1 antibody. Arrow indicates a large branch of superior mesenteric artery or superior mesenteric vein being supplied to the small intestine in the wild-type mesentery. "du" represents duodenum; "p," the proximal part of mid-gut loop; and "dm," the distal part of mid-gut loop.
Figure 4:
FIG. 4 is a photograph showing defects of gastrointestinal blood vessels at the cross-sections of mesentery in the wild-type CXCR4$^{-/-}$ embryo at E13.5, resulting from immunohistostaining of the mesentery and intestine with the anti-PECAM-1 antibody. "a" represents artery, and "v" vein.
Figure 5:
FIG. 5 is a photograph showing defects of gastrointestinal blood vessels in the jejunum in a wild-type CXCR4$^{-/-}$ embryo at E17.5, resulting from immunohistostaining of the mesentery and intestine with the anti-PECAM-1 antibody. Arrow indicates a large branch of superior mesenteric artery or superior mesenteric vein being supplied to the small intestine in the wild-type mesentery.
Figure 6:
FIG. 6 is a photograph showing defects of gastrointestinal blood vessels at the more distal part of the jejunum in the wild-type CXCR4$^{-/-}$ embryo at E17.5, resulting from immunohistostaining of the mesentery and intestine with the anti-PECAM-1 antibody. Arrow indicates a large branch of superior mesenteric artery or superior mesenteric vein being supplied to the small intestine in the wild-type mesentery.
Figure 8:
FIG. 8 is a photograph showing defects of gastrointestinal blood vessels at the cross-sections of mesentery in the mutant CXCR4$^{-/-}$ embryo at E13.5, resulting from immunohistostaining of the mesentery and intestine of the mutant with the anti-PECAM-1 antibody.
Figure 9:
FIG. 9 is a photograph showing defects of gastrointestinal blood vessels in the jejunum in a mutant CXCR4$^{-/-}$ embryo at E17.5, resulting from immunohistostaining of the mesentery and intestine of the mutant with the anti-PECAM-1 antibody.
Figure 11:
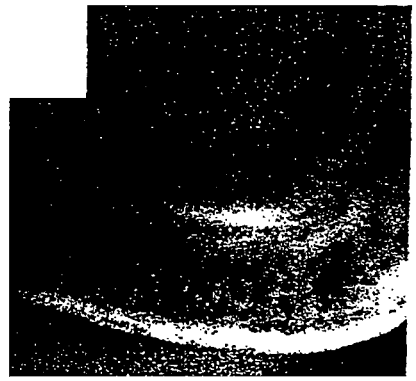
FIG. 11 is a photograph showing defects of gastrointestinal blood vessels, which are a haemorrhagic lesion of the unstained intestine of a mutant mouse, an E16.5 mutant CXCR4$^{-/-}$ embryo, resulting from immunohistostaining of the mesentery and intestine of the mutant with the anti-PE-CAM-1 antibody.

Consequently, in the gastrointestinal tract, including stomach, intestine and mesentery, a highly branched homogeneous vascular network was observed in both the wild-type and the mutant by E11.5. The formation of large and small vessels through remodeling in the mesentery connecting to mid-gut loop was observed at around E12.5. As FIG. 3 shows, many large branches of superior mesenteric artery and vein supplying nutrient to the intestine were formed in wild-type embryos at E13.5. On the other hand, these large branches were not present in the mesenteries of CXCR4$^{-/-}$ embryos at E13.5; instead, only small vessels were formed. Histological analysis by microscopy revealed superior mesenteric arteries and veins in the mesenteries of wild-type embryos at E13.5. This showed that the branched vessels were paired between the artery and the vein (FIG. 4). In contrast, most of the vessels in CXCR4$^{-/-}$ embryos were not paired, but were single, as can be seen in FIG. 8. However, the superior mesenteric arteries and veins within the mesenteries of the wild-type embryos were normal. In E17.5 wild-type embryos, the large mesenteric vessels split into many branches and reach the intestine (FIGS. 5 and 6). However, in the CXCR4$^{-/-}$ embryos such vessels corresponding to the large mesenteric vessels were substantially absent (FIGS. 6 and 9). Also, a few large vessels with aberrant branching were observed in the mutant mesenteries (FIGS. 6 and 9). In most of E16.5 mutant embryos multiple haemorrhagic lesions were observed in their small intestines because of such defective vascular system. This pathogenesis is believed to be the result of aberration of the circulatory system governing the intestine (FIG. 11).

The above-mentioned results have demonstrated that CXCR4 is essential for the normal vascularization of the small intestine: the mechanism is believed to be due to that CXCR4 is involved in the branching and/or remodeling of the mesenteric vessels.

Figure 12A:
FIG. 12A is a photograph showing the result of immunohistostaining the stomach of an E13.5 wild-type with the anti-PECAM-1 antibody. Arrow indicates a large vessel only seen in the wild-type.
Figure 12B:
FIG. 12B is a photograph showing the result of immunohistostaining the stomach of an E13.5 mutant with the anti-PECAM-1 antibody.
Figure 12C:
FIG. 12C is a photograph showing the result of immunohistostaining the stomach of an E15.5 wild-type with the anti-PECAM-1 antibody. Inset in the photograph shows haematoxylin and eosin-stained sections of large vessels in the wall of stained stomach at E15.5. Arrow indicates a large vessel only seen in the wild-type.
Figure 12D:
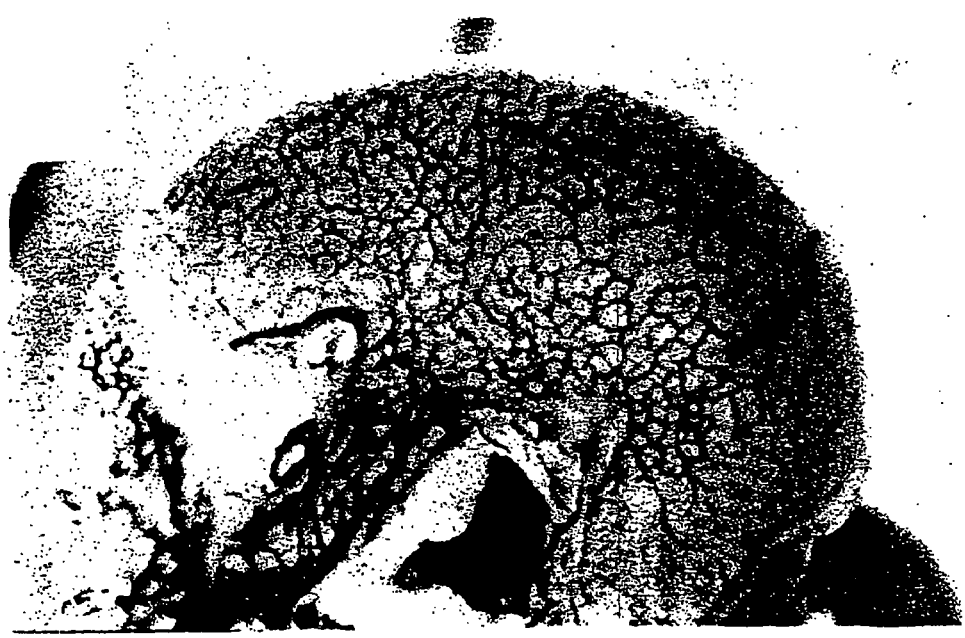
FIG. 12D is a photograph showing the result of immunohistostaining the stomach of an E15.5 mutant with the anti-PECAM-1 antibody.

In the stomach, large vessels branching out from mesenchymal vessels along the lesser curvature were formed and distributed to the entire ventral and dorsal surfaces in the wild-type embryos by E13.5 (FIGS. 12A and 12C). Histological analysis revealed that these vessels were paired between the artery and the vein in the E15.5 wild-type mice as the inset in FIG. 12C shows. However, the corresponding vessels were not found in the mutant embryos (FIGS. 12B and 12D). Formation of the network of small vessels that surrounds the stomach seemed to be normal in the mutant embryos (FIG. 12D).

Histological analysis of the stomachs and intestines of E18.5 mutant embryos detected no obvious abnormalities in organogenesis. For example, the smooth muscle layers (both the outer and inner layers) of the gastrointestinal tract of mutant mice seemed to be normal in the longitudinal and vertical directions.

Figure 7:
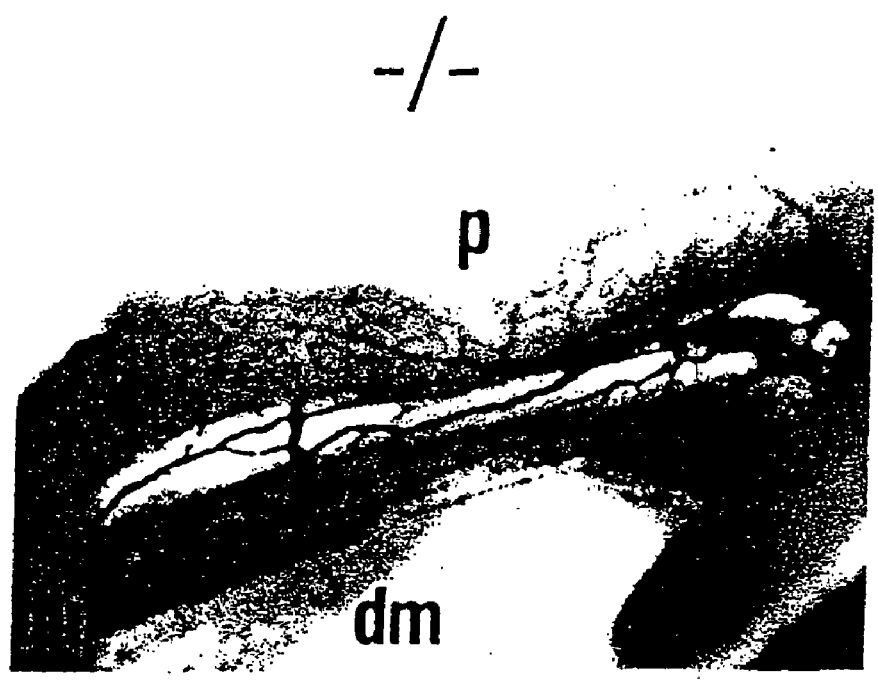
FIG. 7 is a photograph showing defects of gastrointestinal blood vessels at the mesentery and mid-gut loop regions in a mutant CXCR4$^{-/-}$ embryo at E13.5, resulting from immunohistostaining of the mesentery and intestine of mutant with the anti-PECAM-1 antibody. "p" represents the proximal part of mid-gut loop; and "dm," the distal part of mid-gut loop.

FIGS. 3-6 are photographs showing defects of the gastrointestinal vessels in the CXCR4$^{-/-}$ embryos, and also photographs showing immunohistostaining of mesenteries and intestines of the wild-types with the anti-PECAM antibody. FIG. 3 shows the mesentry and mid-gut loop regions at E13.5. FIG. 5 shows a jejunum at E17.5. FIG. 6 shows a jejunum at E17.5. FIG. 7 shows a cross-section of the stained mesentry at E13.5. The arrows in FIGS. 3, 5, and 6 indicate large branches of superior mesenteric artery or superior mesenteric vein supplying nutrient to the small intestine, in wild-type mesentries.

Figure 10:
FIG. 10 is a photograph showing defects of gastrointestinal blood vessels at a more distal part of the jejunum in the mutant CXCR4$^{-/-}$ embryo at 17.5, resulting from immunohistostaining of the mesentery and intestine of the mutant with the anti-PECAM-1 antibody.

Similarly, FIGS. 7-11 are photographs showing defects of the gastrointestinal vessels in the CXCR4$^{-/-}$ embryos, and also photographs showing immunohistostaining of mesenteries and intestines of the mutants with the anti-PECAM antibody. FIG. 7 shows the mesentry and mid-gut loop regions at E13.5. FIG. 9 shows a jejunum at E17.5. FIG. 10 shows a jejunum at E17.5. FIG. 7 shows a cross-section of the stained mesentry at E13.5. FIG. 11 shows the haemorrhagic lesions of unstained intestine of a mutant mouse at E16.5. The arrows in FIGS. 9 and 10 indicate large vessels displaying aberrant running and/or branching in the mutant mice.

FIGS. 12A-12D are photographs showing the results of immunohistostaining stomachs with the anti-PECAM antibody. FIGS. 12A and 12B show E13.5; FIGS. 12C and 12D show E15.5; FIGS. 12A and 12C show the wild types; and FIGS. 12B and 12D show the mutants. The inset in the photograph of FIG. 12C shows a haematoxylin-and-eosin-stained section of large vessels in the wall of stained stomach at E15.5. The arrows in FIGS. 12A and 12C indicate large vessels only observed in the mutant. "du" represents duodenum; "p" represents the proximal part of mid-gut loop; "dm" represents the distal part of mid-gut loop; "a" represents artery; and "v" represents vein.

These findings indicate that the abnormalities in vascularization in the CXCR4$^{-/-}$ mice are not a secondary outcome of those in the gastrointestinal tracts themselves. Abnormalities similar to those in vascularization were also observed in the mice lacking PBSF/SDF-1.

In situ hybridization analysis indicated that CXCR4 transcripts were expressed in the endothelial cells of blood vessels in the mesentery and in the wall of the intestine and stomach in the E12.5 wild-type embryos (FIGS. 13B and 13E). Particularly, strong expression was observed in the endothelial cells of branches arising from the superior mesenteric arteries (FIGS. 13B and 13E). In contrast, PBSF/SDF-1 was expressed at high levels in mesenchymal cells surrounding the endothelial cells of the mesentry, but not in the endothelial cells or the wall of intestine and stomach (FIG. 13C).

FIGS. 13A-13F are photographs showing an analysis of CXCR4 and PBSF/SDF-1 expression in the gastrointestinal tract through in situ hybridization. Serial sections of the wild-type mesentery connecting to the mid-gut loop were used; one piece was stained with haematoxylin and eosin (FIGS. 13A and 13D); another piece was hybridized to the CXCR4-specific probe (FIGS. 13B and 13E); an additional piece was hybridized to the PBSF/SDF-1-specific probe (FIG. 13E). FIGS. 13D and 13E are enlargements of branched vessels arising from the superior mesenteric artery shown in FIGS. 13A and 13B, indicating strong expression of CXCR4 in endothelial cells of the vessel. The arrows and arrowheads in FIGS. 13B and 13E indicate the endothelial cells of mesenteric blood vessels with observed CXCR4 expression. PBSF/SDF-1 is expressed in the mesenchymal cells surrounding endothelial cells in the mesentery (FIG. 13E). FIG. 13F is a cross-section of bone marrow of the E18.5 wild-type embryo, showing CXCR4 expression in haemotopoietic cells but not in spindle-shaped stromal cells. "m" represents mesentry; "i" represents intestine; "a" represents superior mesenteric artery; and "v" represents superior mesenteric vein.

The expression patterns obtained indicate that PBSF/SDF-1 produced by mesenchymal cells acts on CXCR4 on endothelial cells; and this strongly suggests the presence of the paracrine signal by a cytokine that plays a extremely important role in the mesenteric mesenchyme. Thus, the phenotype that lacks large vessels in the stomachs of CXCR4$^{-/-}$ and PBSF/SDF-1$^{-/-}$ may result from abnormalities in the vascular branching and/or remodelling in the mesenchyme along the lesser curvature of the stomach.

To examine the vascular systems of other organs, a whole-mount yolk sac, brain and heart were stained with an anti-PECAM-1 monoclonal antibody. There was no obvious difference between CXCR4$^{-/-}$ and PBSF/SDF-1$^{-/-}$, and the wild-type in the formation of large and small vessels in the whole-mount yolk sac (E12.5, E14.5), the head region (E11.5) and the heart (E12.5-E14.5).

In summary, the aforementioned experimental results have shown that CXCR4 and PBSF/SDF-1 are essential for the formation of a mature vascular system which is supplied to the gastrointestinal tract by acting on the endothelial cells of blood vessels and regulating vascular branching and/or remodelling.

A flow cytometric analysis revealed that the number of B-cell progenitors in fetal livers of CXCR4 mice was severely reduced. Histological analysis did not detect myelocytes and their progenitors in the medullary cavity. In addition, defects of the membranous portion of the cardiac ventricular septum were found in the hearts of E18.5 mutant mice. These abnormalities are very similar to the phenotype found in the mice lacking PBSF/SDF-1, supporting the thinking that CXCR4 is a primary physiological receptor for PBSF/SDF-1.

In the E18.5 wild-type embryonic bone marrow as determined by in situ hybridization, CXCR4 transcripts were expressed in hematopoietic cells, while they were not expressed in spindle-shaped stroma cells where the expression of PBSF/SDF-1 transcripts had been observed (FIG. 3D). The results of these expression patterns mean the presence of paracrine signaling in bone marrow.

Analyses of receptor tyrosine kinases (RTKS), such as Flk-1 and Tie-2, and their ligands, such as VEGF, angiopoietin-1 and PDGF-B that have hitherto been reported, using mutant mice have indicated that they play an important role in development of the vascular system, and that many of them are required for the very early stage of vascularization in genesis as well as for vascularization in all parts of body, including the york sac and the extra-embryonic vasculature. (Shalaby, F. et al., Nature 376, 62-66 (1995); Fong, G.-H., Rossant, J., Gertsenstein, M. & Breitman, M. L., Nature 376, 66-70 (1995); Dumount, D. H. et al., Genes Dev 8, 1897-1909 (1994); Sato, T. N. et al., Nature, 376, 70-74 (1995); Carmeliet, P. et al., Nature, 880, 435-439 (1996); Ferrara, N. et al., Nature, 380, 439-442 (1996); and Suri, C. et al., Cell 87, 1171-1180 (1996)).

In contrast, the functions of CXCR4 and PBSF/SDF-1 operate at later stages of genesis and are organ-specific. Tie-2 and its ligand, angiopoietin-1, are thought to be necessary for the branching and/or remodelling in the early vascular system. (Sato, T. N. et al., Nature 376, 70-74 (1995); Suri, C. et al., Cell 87, 1171-1180 (1996)). Their roles in the formation of the mature vascular system in the gastrointestinal tract are not clear. Obvious abnormalities found in the York sac vascular system of Tie-2 or angiopoietin-1$^{-/-}$ mice were not noted in the CXCR4 or PBSF/SDF-1$^{-/-}$ mice. CXC chemokines, such as PF4 (Maione, T. E. et al., Science 247, 77-79 (1990)), IL-8 (Koch, A. E. et al., Science 258, 1798-1801 (1992)), IP-10 (Luster, A. D. et al., J. Exp. Med. 182, 219-231 (1995)), and Groβ (Cao, Y. H., et al., J. J. Exp. Med. 182, 2069-2077 (1995)), have been reported to be neovascularization regulators. However, expression of their receptors in endothelial cells and their physiological roles have not yet been elucidated. Although coagulation factor V (Cui, J., et al., Nature, 384, 66-68 (1996)) and tissue factor (Carmeliet, P. et al., Nature 883, 75-78 (1996)) have been shown to be essential for the york sac vascular system, it is not clear as to what kind of acceptor mediates these factors.

With the background mentioned above, it can be said that this invention have demonstrated the presence of a novel signaling system—chemokines and a seven-transmembrane spanning, G-protein-coupled receptors—essential for vascularization.

It has recently been shown that mice lacking the α-subunit of the heterotrimeric GTP-binding protein Gα13 have abnormalities, such as no formation of a york-sac vascular system and enlargement of embryonic small vessels. Although the phenotypes are different from those of mice lacking CXCR4, it is necessary to examine the possibility of CXCR4's coupling to Gα13.

It is known that CXCR4 and CCR5 are essential co-receptors when T-cell line tropic and macrophage-tropic HIV-1 strains infect host cells, respectively. (Feng, Y., et al., Science 272, 872-877 (1996); Fauci, A. S., Nature 884, 529-584 (1996)). Between the two, the people homozygous for CCR5 deletion have been discovered; and they are resistant to HIV-1 infection and have no obvious health problems. (Liu, R et al., Cell 86, 367-377 (1996); Samson., M. et al., Nature 382, 722-725 (1996); and Dean, M. et al., Science 273, 1856-1861).

Concerning the other CXCR4, it has, however, been strongly suggested that homologous CXCR4 deletion is unlikely to occur in humans since mice lacking CXCR4 are apt to die in utero. There still remains the possibility that additional genetic factors or homologous viable mutations may exist in long-term survivors who are resistant to T cell-line-tropic HIV-1.

INDUSTRIAL APPLICABILITY

Based on the finding of this invention that vascularization is suppressed in CXCR4 knockout mice, a vascularization inhibitor comprising as the effective ingredient, a substance that inhibits the action of CXCR4 can be prepared: since vascularization is essential for the maintenance and enlargement of cancerous tissues, the finding is utilized in the preparation of an anti-solid cancer agent and a therapeutic agent for a disease pathologically caused by neovascularization, which comprises as the effective ingredient a substance that inhibits the action of CXCR4, as well as in the preparation of a tissue-repairing agent comprising as the effective ingredient, a substance that potentiates the action of CXCR4.

---

The invention claimed is:

1. A method for treating a solid tumor comprising administering an anti-human CXCR4 antibody or a fragment thereof that inhibits binding of SDF-1 to human CXCR4, to a human subject expressing CXCR4 in need thereof, wherein the anti-human CXCR4 antibody or fragment thereof inhibits growth of, or reduces the size of, the solid tumor.

2. The method of claim 1, wherein the anti-human CXCR4 antibody or fragment thereof binds to the region of human CXCR4 which interacts with SDF-1.

3. A method for treating a disease pathologically caused by neovascularization comprising administering an anti-human CXCR4 antibody or a fragment thereof that inhibits binding of SDF-1 to human CXCR4, to a human subject expressing CXCR4 in need thereof, wherein the anti-human CXCR4 antibody or fragment thereof inhibits neovascularization.

4. The method of claim 3, wherein the anti-human CXCR4 antibody or fragment thereof binds to the region of human CXCR4 which interacts with SDF-1.

5. A method for suppressing vascularization comprising administering an anti-human CXCR4 antibody or a fragment thereof that inhibits binding of SDF-1 to human CXCR4, to a human subject expressing CXCR4 in need thereof, wherein the anti-human CXCR4 antibody or a fragment thereof inhibits vascularization.

6. The method of claim 5, wherein the anti-human CXCR4 antibody or fragment thereof binds to the region of human CXCR4 which interacts with SDF-1.

* * * * *